(12) United States Patent
Woloszko et al.

(10) Patent No.: US 11,116,569 B2
(45) Date of Patent: Sep. 14, 2021

(54) ELECTROSURGICAL SYSTEMS AND METHODS

(71) Applicant: Smith & Nephew, Inc., Memphis, TN (US)

(72) Inventors: Jean Woloszko, Austin, TX (US); Jonathan Gaspredes, Austin, TX (US); Douglas G. Evans, Austin, TX (US); Robert Lathrop, Medford, MA (US); Brendan Smith, Austin, TX (US); David Turner, Austin, TX (US); Christopher J. Aholt, Austin, TX (US); Troy S. Hemme, Minneapolis, MI (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 16/613,730

(22) PCT Filed: May 16, 2018

(86) PCT No.: PCT/US2018/032989
§ 371 (c)(1),
(2) Date: Nov. 14, 2019

(87) PCT Pub. No.: WO2018/213461
PCT Pub. Date: Nov. 22, 2018

(65) Prior Publication Data
US 2020/0397500 A1    Dec. 24, 2020

Related U.S. Application Data

(60) Provisional application No. 62/506,870, filed on May 16, 2017.

(51) Int. Cl.
*A61B 18/14*    (2006.01)
*A61B 18/04*    (2006.01)
(Continued)

(52) U.S. Cl.
CPC .......... *A61B 18/148* (2013.01); *A61B 18/042* (2013.01); *A61B 18/1233* (2013.01);
(Continued)

(58) Field of Classification Search
CPC . A61B 18/148; A61B 18/042; A61B 18/1233; A61B 2018/00577;
(Continued)

(56) References Cited

U.S. PATENT DOCUMENTS

2004/0030330 A1*  2/2004  Brassell ............ A61B 18/1206
                                                                  606/41
2014/0236141 A1*  8/2014  Woloszko .......... A61B 18/1233
                                                                  606/34
(Continued)

FOREIGN PATENT DOCUMENTS

EP    2928402    10/2015

OTHER PUBLICATIONS

Search Report and Written Opinion for PCT application No. PCT/US2018/032989 dated Sep. 4, 2018, 13 pages.

*Primary Examiner* — Eun Hwa Kim
*Assistant Examiner* — Catherine Premraj
(74) *Attorney, Agent, or Firm* — Norman F. Hainer, Jr.

(57) ABSTRACT

An electrosurgical wand is disclosed for treating a plurality of tissues at a variety of tissue locations. The electrosurgical wand includes a handle on a proximal end and an elongate shaft with a combination active electrode at the distal end. The combination active electrode includes with a blade and screen portion; the blade portion extending along and laterally from the wand longitudinal axis, forming a dissecting tip. The screen portion extends from the blade portion at an obtuse angle and has at least one aspiration aperture through it. The wand also includes a second and third electrode, proximally spaced from the combination active electrode.

(Continued)

The second electrode spans a portion of an outside surface of the wand adjacent the blade portion, while the third electrode spans a portion of the outside surface of the wand opposite the second electrode.

14 Claims, 14 Drawing Sheets

(51) Int. Cl.
  *A61B 18/12* (2006.01)
  *A61B 18/00* (2006.01)
(52) U.S. Cl.
  CPC .............. *A61B 2018/0063* (2013.01); *A61B 2018/0091* (2013.01); *A61B 2018/00577* (2013.01); *A61B 2018/00601* (2013.01); *A61B 2018/00607* (2013.01); *A61B 2018/00625* (2013.01); *A61B 2018/00767* (2013.01); *A61B 2018/122* (2013.01); *A61B 2018/126* (2013.01); *A61B 2018/1412* (2013.01); *A61B 2018/1467* (2013.01); *A61B 2218/002* (2013.01); *A61B 2218/007* (2013.01)
(58) Field of Classification Search
  CPC ........... A61B 2018/00601; A61B 2018/00607; A61B 2018/00625; A61B 2018/0063; A61B 2018/00767; A61B 2018/0091; A61B 2018/122; A61B 2018/126; A61B 2018/1412; A61B 2018/1467; A61B 2218/002; A61B 2218/007
  See application file for complete search history.

(56) References Cited

U.S. PATENT DOCUMENTS

| | | |
|---|---|---|
| 2014/0276201 A1 | 9/2014 | Woloszko et al. |
| 2014/0276725 A1 | 9/2014 | Cox et al. |
| 2014/0336630 A1* | 11/2014 | Woloszko ............ A61B 18/148 606/34 |
| 2014/0336640 A1* | 11/2014 | Beeckler ............ A61B 18/1492 606/41 |

* cited by examiner

ELECTROSURGICAL SYSTEMS AND METHODS

CROSS-REFERENCE TO RELATED APPLICATIONS

This application is a U.S. National Phase Entry of PCT Application Serial No. PCT/US18/032989 filed May 16, 2018 and titled "ELECTROSURGICAL SYSTEMS AND METHODS." The PCT application claims priority to and benefit of U.S. Provisional Application No. 62/506,870, filed May 16, 2017, the contents of which are incorporated herein by reference in their entirety for all purposes.

BACKGROUND

Radiofrequency (RF) energy is used in a wide range of surgical procedures because it provides efficient tissue resection and coagulation and relatively easy access to the target tissues through a portal or cannula. More complex clinical procedures generally require electrosurgical devices that can provide a variety of functions and configurations, which can sometimes be problematic. These clinical procedures may include treating various tissue types, located at differing access angles along narrow anatomies, as well as differing tissue effects. Solutions generally require a plurality of electrosurgical devices. These more complex procedures arise generally in otolaryngological, arthroscopic, arthroplasty, general and spinal procedures. In addition, conventional electrosurgical devices tend to operate at high tissue temperatures, and may induce much tissue damage with postoperative tissue necrosis and degeneration of the remaining tissues described as a side effect. Molecular dissociation using an ionized vapor layer (such as COBLATION® brand products available from Smith & Nephew, Inc.) has been reported to operate at lower temperatures and possibly reduce tissue damage.

Accordingly, improved systems and methods are still desired for precise tissue removal in narrow anatomies via low temperature electrosurgical treatment of tissue. In particular, improved systems including a single device that accesses narrow anatomies in a variety of locations, and provides a plurality of tissue treatment modes or varying levels of coagulation would provide a competitive advantage.

SUMMARY

Various embodiments described herein are directed to a method and a system that enables a single handpiece to provide a broad range of effects by combining plasma surgery, thermal electrodes and bipolar coagulation using saline delivery. Some embodiments may include a dual RF generator in conjunction with a handpiece with at least three electrodes. Such systems may be used for various open surgical applications, including ear nose and throat (ENT) surgery and also for soft tissue management during total or partial knee or hip arthroplasty.

An electrosurgical wand is disclosed including a handle on a proximal end of the electrosurgical wand and an elongate shaft coupled to the handle and extending distally from the handle along a longitudinal axis. The wand also includes a combination active electrode having a blade and screen portion disposed on a distal end of the wand, wherein the blade portion extends along and laterally from the wand longitudinal axis defining the distal-most portion of the wand, while the screen portion forms an obtuse angle to the blade portion, the obtuse angle opening toward the distal end of the wand and has at least one aperture therein in operational relationship to an aspiration channel within the wand. The wand also includes second and third electrodes, proximally spaced from the combination active electrode, the second electrode spanning a portion of an outside surface of the wand adjacent and proximally spaced from and blade portion of the combination active electrode, the third electrode spanning a portion of the outside surface of the wand opposite the second electrode. In some embodiments, the second electrode defines a thermal electrode in that it forms a portion of the current return path with the active electrode, while providing some thermal effects at the second electrode so as to provide some hemostasis adjacent the second electrode. In some embodiments, the second and third electrodes define two distinct exposed portions of a single element, the exposed portions being separated by an insulative spacer and insulative sheath. The second electrode may span a single side of the wand, and the third electrode may span at least three sides of the wand and have a larger surface area than the second electrode. The second and third electrodes may be axially offset from each other, such that a distal edge of the second electrode may extend further axially than a distal edge of the third electrode, so that the distal edges of the second and third electrodes lie along a plane that is parallel to the active electrode screen portion. This may help to keep a more uniform tissue effect around the active electrode.

In some embodiments, the screen portion further comprises one or more surface asperities configured to more readily form plasma adjacent the surface asperity. The second electrode may have a plurality of axially spaced apertures therethough, and the third electrode may also include a plurality of radially spaced apertures therethrough. At least some of the apertures are fluidly coupled to a fluid delivery channel within the wand that is fluidly coupled to a source of electrically conductive fluid. In some embodiments, the second electrode has a polished surface finish configured to reduce tissue sticking, and the third electrode has a rougher or unpolished surface finish, configured to improve fluid retention on its surface. Good fluid retention may provide a larger surface of wetted return electrode and thereby an improved, more uniform and more consistent plasma generation around the active electrode.

A system is also disclosed including an electrosurgical controller with a processor, a memory coupled to the processor, a voltage generator operatively coupled to the processor, the voltage generator comprising an active and return terminal and a wand connector configured to couple to a connector of an electrosurgical wand, and the wand connector comprising a plurality of electrical pins, and at least one electrical pin coupled to the active terminal of the voltage generator. The system also includes a peristaltic pump comprising a rotor coupled to an electric motor, the electric motor operatively coupled to the processor. The system also includes an electrosurgical wand with a handle, an elongate shaft extending distally from the handle along a longitudinal central axis and a combination active electrode disposed at a distal end of the electrosurgical wand. The combination active electrode has a blade portion at the distal-most end of the electrosurgical wand extending along and laterally from the longitudinal central axis and also a screen portion with at least one aspiration aperture through it, in operational relationship to a fluid channel within the wand. The wand also includes a return electrode encircling a portion of the elongate shaft and extending along and annularly about the longitudinal central axis, that is split towards the distal end so as to form a first and second exposed portion that are distinct from each other. The first exposed portion extends along a first side of the elongate shaft adjacent the blade portion of the active electrode and the second exposed portion extends along an opposing side of the elongate shaft. The memory stores a program that, when executed by the processor, causes the processor to implement at least two modes of ablation during an electrosurgical procedure. In the first mode of operation, the processor controls flow of fluid though an aperture on the distal end of the electrosurgical wand at a first flow rate, the aperture proximate to the return electrode and also control energy delivered to the combination active electrode by the electrosurgical controller so as to molecularly dissociate tissue with minimal hemostasis. In the second mode of operation, the processor controls a flow of fluid through the aperture at a second flow rate different than the first flow rate and also control the energy delivered by the electrosurgical controller so as to molecularly dissociate tissue with more hemostasis. In some embodiments, the processor controls the energy so as to molecularly dissociate tissue further comprises modulating the voltage generator output between a voltage sufficient to form an ionized vapor layer at the combination active electrode and a voltage sufficient to extinguish the ionized vapor layer at the active electrode. In some embodiments, the processor controls the energy so as to modulate the voltage at a first rate in the first mode and at a second rate that is different than the first rate in the second mode.

A method of treating a plurality of tissues with an electrosurgical wand is also described, including positioning the electrosurgical wand in a first orientation so that a blade portion of a combination active electrode and a first exposed surface of a return electrode of the electrosurgical wand is adjacent a first target tissue. The blade portion is disposed at the distal-most end of the combination active and extends along and laterally from a wand longitudinal central axis. The first exposed surface of the return electrode spans across an outer portion of an elongate shaft of the electrosurgical wand. While the wand is in the first orientation the method further includes applying electrical energy between the combination active electrode and the return electrode so as to concomitantly ablate and thermally treat a target tissue. Ablation is performed by forming, responsive to the energy, localized plasma proximate to the blade portion, so as to molecularly dissociate a portion of the first target tissue from a tissue bed. Thermally treating the tissue provides hemostasis of the tissue bed adjacent the first exposed surface of the return electrode. The method further includes placing the electrosurgical wand in a second orientation, such that a screen portion of the combination active electrode, the first exposed surface of a return electrode and a second exposed surface are all adjacent a second target tissue such that a current path is formed between the active electrode, first and second exposed surface. The first and second exposed surfaces are both distinct from each other. While the electrosurgical wand is in the second orientation the method includes applying electrical energy between the combination active electrode and the return electrode and debulking a portion of the second target tissue. Debulking is achieved by forming, responsive to the energy, localized plasma proximate to both the blade portion and screen portion of the combination active electrodes and ablating the second target tissue. In the second orientation, the first and second exposed surface of a return electrode may be substantially equidistant from the second target tissue configured to promote a more uniform plasma generation across both the blade and screen portion. The method may also include flowing an electrically conductive fluid over the first exposed surface of the electrosurgical wand and towards the active electrode at a first flow rate while the electrosurgical wand in in the first orientation and flowing an electrically conductive fluid over the first and second exposed surface of the electrosurgical wand at a second fluid flow rate, different than the first flow rate in the second orientation. The method may also include adjusting an output associated with the electrical energy while the electrosurgical is in the first orientation so as to apply a modulated electrical energy sufficient to form intermittent localized plasma interspersed with periods of time with resistive heating proximate to the blade portion and concomitantly form a thermal effect adjacent the first exposed surface of the return electrode. Before placing the electrosurgical wand in a second orientation, the elongate shaft may be bent so as to improve access to the second target tissue. The first target tissue may be tonsil tissue and the second target tissue may be adenoid tissue.

Various embodiments described below are useful for sealing larger arterial vessels, e.g., of the order of 1 mm or greater. In some embodiments, high frequency energy is provided in an ablation mode and a coagulation mode to either the same or a different electrode terminal of the controller. In this example, ablation mode defines a first voltage sufficient to effect molecular dissociation or disintegration of the tissue and coagulation mode defines a second, lower voltage sufficient to achieve hemostasis of severed vessels within the tissue and may also allow an ionized vapor adjacent an electrode to extinguish. In other embodiments, an electrosurgical probe is provided having one or more coagulation electrode(s) configured for sealing a vessel, such as an arterial vessel, and one or more ablating electrode(s) configured for either contracting the collagen fibers within the tissue or ablating the tissue. In some embodiments, the coagulation electrode(s) may be configured such that a single voltage can be applied to coagulate with the coagulation electrode(s), and to ablate tissue with the ablation electrode(s). In other embodiments, the power supply is combined with the probe such that the coagulation electrode is used when the power supply is in the coagulation mode (low voltage), and the ablating electrode(s) are used when the power supply is in the ablation mode (higher voltage).

At least some of the various embodiments combine the benefits of these embodiments into one single product, and therefore should provide an ease of use and cost savings for the practitioners and the institutions.

BRIEF DESCRIPTION OF THE DRAWINGS

For a detailed description of example embodiments, reference will now be made to the accompanying drawings in which.

DEFINITIONS

Figure 1:
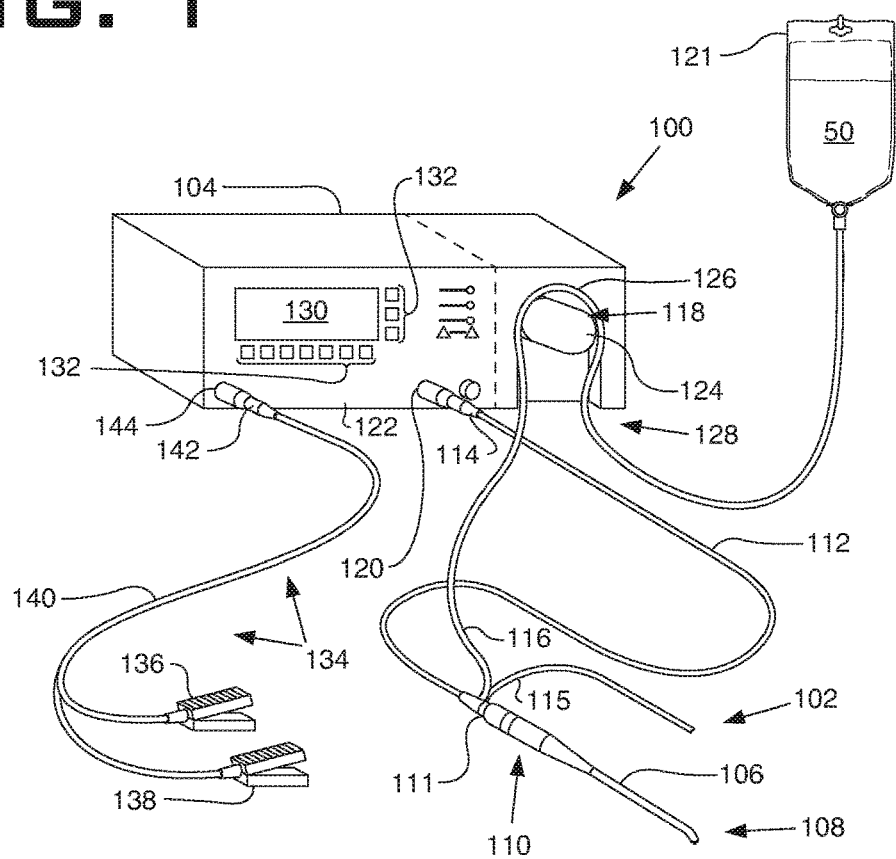
FIG. 1 shows an electrosurgical system in accordance with at least some embodiments of the disclosure.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

Reference to a singular item includes the possibility that there are plural of the same items present. More specifically, as used herein and in the appended claims, the singular forms "a," "an," "said" and "the" include plural references unless the context clearly dictates otherwise. It is further noted that the claims may be drafted to exclude any optional element. As such, this statement serves as antecedent basis for use of such exclusive terminology as "solely," "only" and the like in connection with the recitation of claim elements, or use of a "negative" limitation. Lastly, it is to be appreciated that unless defined otherwise, all technical and scientific terms used herein have the same meaning as commonly understood by one of ordinary skill in the art to which this invention belongs.

"Ablation" shall mean removal of tissue based on tissue interaction with plasma.

"Plasma" shall mean a low temperature gas formed of vapor bubbles or a vapor layer that is capable of emitting an ionized discharge.

"Active electrode" shall mean an electrode of an electrosurgical wand which produces an electrically-induced tissue-altering effect when brought into contact with, or close proximity to, a tissue targeted for treatment.

"Return electrode" shall mean an electrode of an electrosurgical wand which serves to provide a current flow path for electrical charges with respect to an active electrode, and/or an electrode of an electrical surgical wand which does not itself produce an electrically-induced tissue-altering effect on tissue targeted for treatment.

"Thermal electrode" shall mean an electrode of an electrosurgical wand which serves to provide a current flow path for electrical charges with respect to a second electrode that may be an active electrode, producing an electrically-induced thermal tissue-altering effect adjacent the thermal electrode on tissue targeted for treatment.

"Pulsing" shall mean a modulated output energy of the AC voltage signal generated and delivered to at least one electrode on the wand, wherein the output energy modulates between an output energy sufficient to form an ionized vapor layer at the at least one electrode and an output energy that allows the ionized vapor layer to extinguish.

"Blending" or "blended cut" shall mean providing tissue cutting with concomitant hemostasis. When in a bipolar mode, this may be achieved with two electrodes of unequal ratio of electrode surface areas in operational relationship with tissue (setting up an active and a thermal electrode), and/or this may include a pulsing output (defined above) between two electrodes (of equal or unequal surface area ratios). Additionally/alternatively a third electrode may be present, and a first energy output defining a first tissue effect may be delivered to a first electrode and a second energy output defining a different tissue effect may be delivered to a second electrode. The first and second energy outputs may include an ablative output, a coagulating output or a pulsing output.

Where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

FIG. 1 shows an electrosurgical system 100 in accordance with at least some embodiments. In particular, the electrosurgical system 100 comprises an electrosurgical wand 102 (hereinafter "wand 102") coupled to an electrosurgical controller 104 (hereinafter "controller 104") for providing high frequency voltage to a target site; and a fluid source 121 for supplying electrically conducting fluid 50 to wand 102 via fluid delivery tube 116. The wand 102 comprises an elongate shaft 106 that defines distal end 108. The elongate shaft 106 further defines a handle 110 at a proximal end 111, where a physician grips the wand 102 during surgical procedures. The wand 102 further comprises a flexible multi-conductor cable 112 housing one or more electrical leads (not specifically shown in FIG. 1), and the flexible multi-conductor cable 112 terminates in a wand connector 114. As shown in FIG. 1, the wand 102 couples to the controller 104, such as by a controller connector 120 on an outer surface of the enclosure 122 (in the illustrative case of FIG. 1, the front surface).

Though not visible in the view of FIG. 1, in some embodiments the wand 102 has one or more internal fluid conduits coupled to externally accessible tubular members. As illustrated, the wand 102 has a flexible tubular member 116, used to deliver electrically conductive fluid to the distal end 108 of the wand. Fluid delivery may be controlled by pump 118, to provide and control a rate of fluid flow supply to wand 102 via delivery tube 116. In accordance with various embodiments, the tubular member 116 couples to a peristaltic pump 118, which peristaltic pump 118 is illustratively shown as an integral component with the controller 104 (i.e., residing at least partially within the enclosure 122 of the controller 104). In other embodiments, an enclosure for the peristaltic pump 118 may be separate from the enclosure 122 for the controller 104 (as shown by dashed lines in FIG. 1), but in any event the peristaltic pump is operatively coupled to the controller 104. The system 100 may also include a vacuum source (not shown) for coupling to a suction or aspiration lumen or tube 115 associated with the wand 102 for aspirating the target site. Alternatively, a second pump (not shown) may be operatively coupled to the aspiration tube 115, so as to control the aspiration rate. The example peristaltic pump 118 comprises a rotor portion 124 (hereafter just "rotor 124") as well as a stator portion 126 (hereafter just "stator 126"). The example flexible tubular member 116 couples within the peristaltic pump 118 between the rotor 124 and the stator 126, and movement of the rotor 124 against the flexible tubular member 116 causes fluid movement toward the discharge 128.

Still referring to FIG. 1, a display device or interface device 130 is visible through the enclosure 122 of the controller 104, and in some embodiments a user may select operational characteristics of the controller 104 by way of the interface device 130 and/or related buttons 132. For example, using one or more of the buttons 132 the surgeon may select among energy ranges or modes for use with the wand 102 during electrosurgical procedures.

In some embodiments the electrosurgical system 100 also comprises a foot pedal assembly 134. The foot pedal assembly 134 may comprise one or more pedal devices 136 and 138, a flexible multi-conductor cable 140 and a pedal connector 142. While only two pedal devices 136 and 138 are shown, one or more pedal devices may be implemented. The enclosure 122 of the controller 104 may comprise a corresponding connector 144 that couples to the pedal connector 142. A physician may use the foot pedal assembly 134 to control various aspects of the controller 104, such as the mode of ablation. For example, pedal device 136 may be used for on-off control of the application of radio frequency (RF) energy to the wand 102. Further, pedal device 138 may be used to control and/or set the mode of operation of the electrosurgical system. For example, actuation of pedal device 138 may switch between ablation mode and coagulation mode, or between pure cut mode with minimal hemostasis and a blended and/or pulsed ablation mode providing varying levels of concomitant hemostasis as will be described later.

The electrosurgical system 100 of the various embodiments implements ablation which employs Coblation® technology. In particular, the assignee of the present disclosure is the owner of Coblation® technology. Coblation® technology involves the application of at least one radio frequency (RF) signal between one or more active electrodes and one or more return electrodes of the wand 102 to develop high electric field intensities in the vicinity of the target tissue. The electric field intensities may be sufficient to vaporize an electrically conductive fluid over at least a portion of the one or more active electrodes in the region between the one or more active electrodes and the target tissue. The electrically conductive fluid may be inherently present in the body, such as blood, or in some cases extracellular or intracellular fluid. In other embodiments, the electrically conductive fluid may be a liquid or gas, such as isotonic saline. In some embodiments, as shown, the electrically conductive fluid is delivered in the vicinity of the active electrode and/or to the target site by a delivery system.

When the electrically conductive fluid is heated to the point that the atoms of the fluid vaporize faster than the atoms recondense, a gas is formed. When sufficient energy is applied to the gas, the atoms collide with each other causing a release of electrons in the process, and an ionized gas or plasma is formed (the so-called "fourth state of matter"). Stated otherwise, plasmas may be formed by heating a gas and ionizing the gas by driving an electric current through the gas, or by directing electromagnetic waves into the gas. The methods of plasma formation give energy to free electrons in the plasma directly, electron-atom collisions liberate more electrons, and the process cascades until the desired degree of ionization is achieved. A more complete description of plasma can be found in Plasma Physics, by R. J. Goldston and P. H. Rutherford of the Plasma Physics Laboratory of Princeton University (1995), the complete disclosure of which is incorporated herein by reference.

As the density of the plasma becomes sufficiently low (i.e., less than approximately 1020 atoms/cm3 for aqueous solutions), the electron mean free path increases such that subsequently injected electrons cause impact ionization within the plasma. When the ionic particles in the plasma layer have sufficient energy (e.g., 3.5 electron-Volt (eV) to 5 eV), collisions of the ionic particles with molecules that make up the target tissue break molecular bonds of the target tissue, dissociating molecules into free radicals which then combine into gaseous or liquid species. By means of the molecular dissociation (as opposed to thermal evaporation or carbonization), the target tissue is volumetrically removed through molecular dissociation of larger organic molecules into smaller molecules and/or atoms, such as hydrogen, oxygen, oxides of carbon, hydrocarbons and nitrogen compounds. The molecular dissociation completely removes the tissue structure, as opposed to dehydrating the tissue material by the removal of liquid within the cells of the tissue and extracellular fluids, as occurs in related art electrosurgical desiccation and vaporization. A more detailed description of the molecular dissociation can be found in commonly assigned U.S. Pat. No. 5,697,882 the complete disclosure of which is incorporated herein by reference.

The energy density produced by electrosurgical system 100 at the distal end 108 of the wand 102 may be varied by adjusting a variety of factors, such as: the number of active electrodes; electrode size and spacing; electrode surface area; asperities and/or sharp edges on the electrode surfaces; electrode materials; applied voltage; current limiting of one or more electrodes (e.g., by placing an inductor in series with an electrode); electrical conductivity of the fluid in contact with the electrodes; density of the conductive fluid; and other factors. Accordingly, these factors can be manipulated to control the energy level of the excited electrons. Since different tissue structures have different molecular bonds, the electrosurgical system 100 may be configured to produce energy sufficient to break the molecular bonds of certain tissue but insufficient to break the molecular bonds of other tissue. For example, fatty tissue (e.g., adipose) has double bonds that require an energy level higher than 4 eV to 5 eV (i.e., on the order of about 8 eV) to break. Accordingly, the Coblation® technology in some modes of operation does not ablate such fatty tissue; however, the Coblation® technology at the lower energy levels may be used to effectively ablate cells to release the inner fat content in a liquid form. Other modes of operation may have increased energy such that the double bonds can also be broken in a similar fashion as the single bonds (e.g., increasing voltage or changing the electrode configuration to increase the current density at the electrodes). A more complete description of the various phenomena can be found in commonly assigned U.S. Pat. Nos. 6,355,032, 6,149,120 and 6,296,136, the complete disclosures of which are incorporated herein by reference.

Generally the intent of the system and varying wand-tip embodiments disclosed is to provide one wand that can provide a broad variety of functions, and may finely dissect or provide a blended cut to a first tissue while in a first configuration, and provide a different tissue effect while in a second configuration. A first example set of embodiments disclosed is configured to dissect a first tissue such as tonsil tissue while in a first configuration, and debulk (rapidly dissociate and remove) adenoids while in a second configuration. A second example set of embodiments disclosed is configured to dissect or cut through a first tissue such as skin or an outer layer while in a first configuration, and coagulate areas adjacent the first tissue while in a second configuration. A first and second configuration may be defined by a change in at least one of the following parameters; the orientation of the wand or angle of approach to the target tissue; a change of the surface areas and geometry of the active electrode in operational relationship with the target tissue or a change of electrodes placed near the target tissue; an alteration of the bend angle(s) along the wand shaft, by deformation; a change in the fluid flow rate delivered to and removed from the wand distal end; alteration of the energy output such as frequency, control mode, voltage or voltage pulses to at least one of the electrodes of the wand. The example systems may also comprise some tri-polar or multipolar wands having at least three electrodes. By way of the controller, each electrode may be interchangeably connected to at least one active and one return terminal of an RF generator of the controller defining the first and second configurations also. Thus, each electrode may be an active electrode, a thermal electrode or a return electrode, or floating for any particular surgical procedure.

As a more specific example, when removing tonsils, the active electrode requires more of a blade- or plate-style electrode (or possibly a needle-style electrode) that extends away from the spacer. An active electrode with a narrow distal tip is configured to form plasma predominantly at the very tip so as to act similarly to a blade and finely dissect tonsil tissue away from fossa. Access to grasp the tonsil is relative easy during a tonsillectomy compared to the adenoid, and so it is preferable to grasp and remove the tonsil using a secondary device, as the active electrode ablates and disconnects the tonsil from the fossa. Significant pain after a tonsillectomy is oftentimes attributed to damage to the remaining tissue bed and so very controlled dissection with limited hemostasis is preferred to manage the patient post-surgery pain. Contrary to that, grasping the adenoid is not as readily available, and so the active electrode is used to gradually dissociate the upper layers of the adenoid and remove these molecularly dissociated layers through an aspiration aperture through the active electrode and thereby debulk the adenoid. The tissue bed under the adenoids is also generally considered less sensitive to heat. Therefore when debulking adenoids, the active electrode may be larger in surface area, the tissue effect may be more aggressive (delivering a higher voltage) and fluid delivery and/or aspiration rates may be higher to enhance debulked tissue removal.

Figure 2:
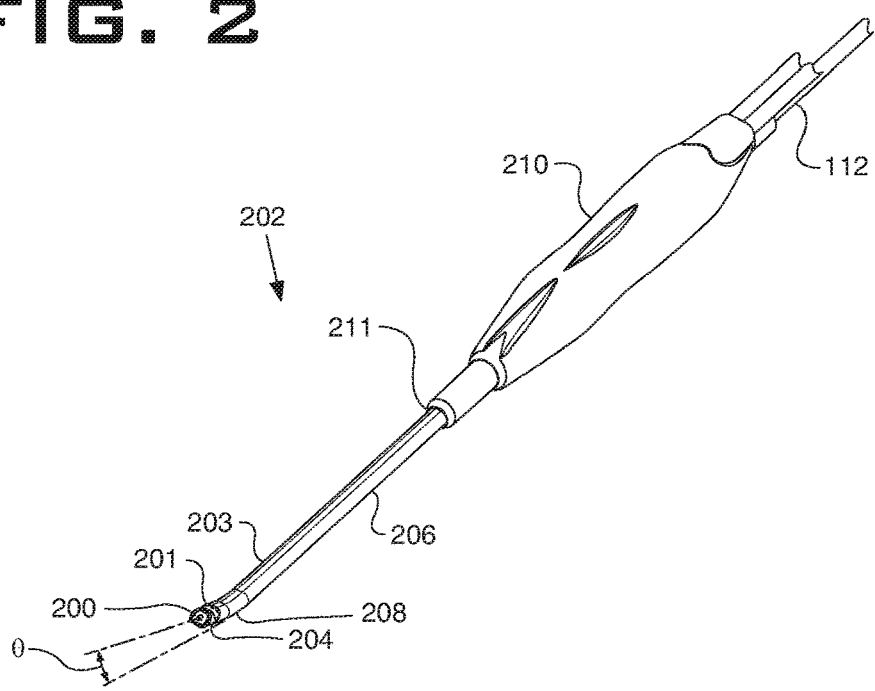
FIG. 2 shows a perspective view of an electrosurgical wand in accordance with at least some embodiments of the disclosure.

FIG. 2 shows a side elevation view of an example wand embodiment 202 in accordance with example systems, configured for tonsil and adenoid removal. The wand 202 comprises elongate shaft 206 which may be somewhat rigid, and a handle 210 coupled to the proximal end 211 of the elongate shaft 206. As shown shaft distal end includes a bend 203, configured to orient the distal-most portion of the wand at a non-zero angle $\Theta$ relative to the shaft longitudinal axis proximal the bend 203, said angle $\Theta$ configured to aid in access to and visibility of the target tissue such as tonsil tissue, and is between 5-45 degrees, and more preferably between 10-30 degrees. In some embodiments, the shaft 206 may be sufficiently malleable so that bend 203 may be altered to better access a target tissue, or a second bend (not shown) may be added adjacent 203. Elongate shaft 206 may therefore comprise a somewhat malleable material, such as annealed stainless steel, so as to readily deform upon manipulation by the clinician. At the distal end 208 resides an active electrode 200, return electrode(s) 201, and an electrode support member 204. The relationship of the various elements at the distal end 208 of the wand 202 will be discussed in greater below. Active electrode 200 may be coupled to an active or passive control network within controller 104 (FIG. 1) by means of one or more insulated electrical connectors (not shown) in the multi-conductor cable 112. The active electrode 200 is electrically isolated from other electrodes on the tip, such as a common or return electrode 201 which is disposed on the elongate shaft 106. Proximally from the distal tip, the return electrode(s) 201 is at least partially concentric with the elongate shaft 106 of the wand 202. The elongate shaft and support member at the distal end define an oblong cross section, preferable so as to allow for a larger aspiration aperture and improve tissue removal during debulking. The support member 204 is positioned distal to and around the return electrode 201 and may be composed of an electrically insulating material such as epoxy, plastic, ceramics silicone, glass or the like. Support member 204 extends from the distal end 208 of elongate shaft 206 (usually about 1 to 20 mm) and provides support for active electrode 202.

Figure 3A:
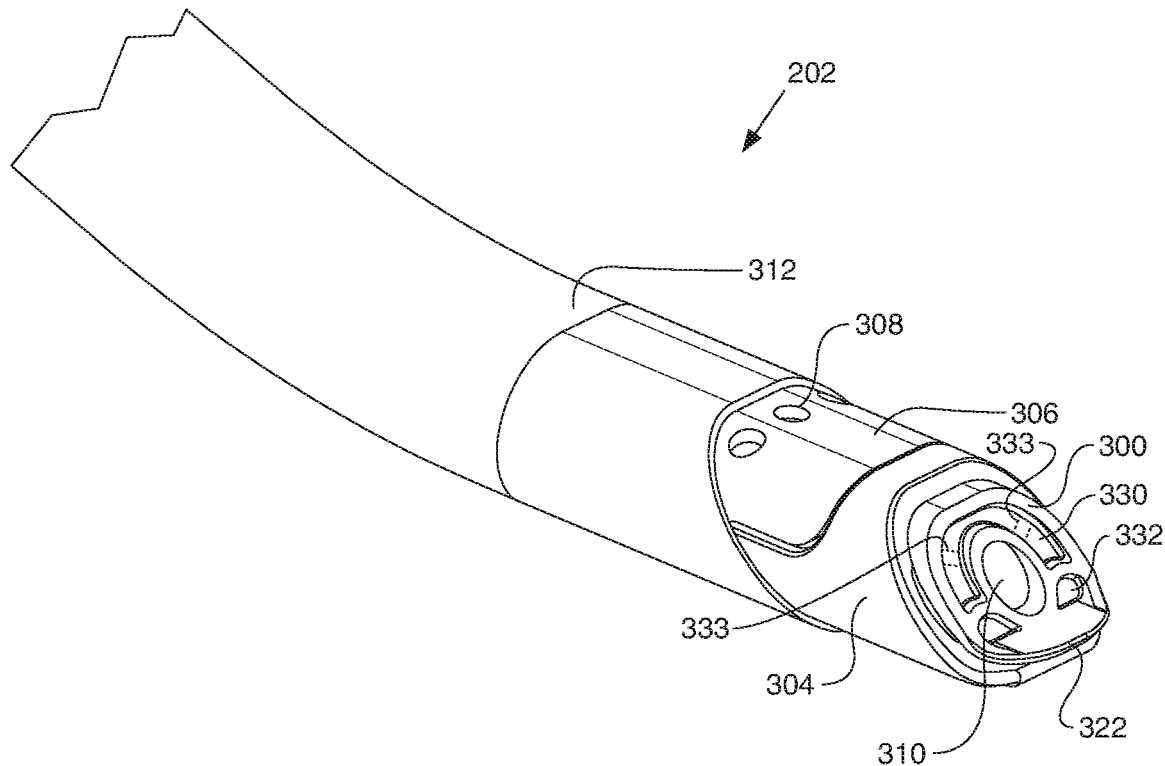
FIG. 3A-3C shows various views of a first wand-tip embodiment in accordance with at least some embodiments of the disclosure.

FIG. 3A shows a perspective view of a wand 202 with a first wand-tip embodiment in accordance with example systems. Visible in FIG. 3A is the active electrode 300 at the distal tip with an aperture 310 therethrough fluidly coupled to the flexible tubular member 115 (seen in FIG. 1) via a fluid delivery element (not shown) disposed along the wand elongate shaft 206. The active electrode 300 is a combination active electrode comprising both a lip or blade portion 322 and a screen portion 320. The blade portion 322 defines the distal-most end of the wand configured to finely dissect tissue from a tissue bed such as tonsil tissue from fossa. It also serves as a leading edge while debulking adenoid tissue and is configured to scoop the adenoid tissue away from the tissue bed and lead it towards the screen portion of the active electrode 300 and aperture 310. Active electrode 300 is coupled to and supported by an insulating spacer 304. Proximal the spacer 304 is a return electrode 306 with fluid delivery apertures 308 therethrough, the apertures 308 fluidly coupled to the flexible tubular member 116 (not shown) via fluid delivery elements disposed along the wand elongate shaft. In the example system, the distal end of the wand 202 is covered with an insulating sheath 312 that not only electrically isolates portions of the distal end of the wand 202, but also may form guard rails to direct fluid flow of electrically conductive fluid out of the apertures 308 over the return electrode 306 and toward the active electrode 300. Best seen in FIG. 3B, insulating sheath 312 also covers a portion of return electrode 306, so as to define a first return electrode exposed portion 306a on the lower-side or underside of wand 202 and second return electrode exposed portion 306b, on the upper-side of wand 202 and wherein the first and second exposed portions 306a and 306b form two discrete portions of the return electrode 306, at the same electrical potential. Stated otherwise the two exposed portions are separated by the spacer 304 and in combination with the sheath 312 provide an insulating means over return electrode 306 so as to effectively "break the circuit" between the two exposed portions 306a and 306b. This directs or isolates the energy flow, enabling the wand-tip to emulate a tripolar-type of performance with a bipolar configuration, by forming three distinct electrically conducting surfaces at the locations shown (active electrode 300, first exposed return electrode portion 306a and second exposed return electrode portion 306b). At least some of the conducting surfaces are inherently selected by orientation of the wand relative to tissues rendering some electrodes in operational relationship with the tissue and some, not so.

Both exposed surfaces of the return electrode 306 have fluid delivery apertures therethrough so that fluid delivery surrounds the wand and active electrode 300, improve wetting and electrical conductivity for coagulation at the distal tip, as well as for uniform plasma formation around the active electrode surface (top and bottom), which may be particularly helpful for adenoidectomy. In addition, as will be explained later, fluid flow over the first exposed portion of the return electrode may also reduce sticking when the return electrode temporarily behaves as a thermal electrode to provide hemostasis. The amount of thermal effect achieved by actively regulating the amount of flow in conjunction with different voltage settings, such that lower flow can lead to less heat and higher flow can create more heating. The inventors have also found that when a broader debulking tissue effect is desired around a larger surface of the active electrode, the wand is frequently oriented such that gravity directs more fluid to flow from the apertures 308a on the underside relative to the apertures 308b on the top side; consequently hindering the desired consistency of plasma generation around the screen portion of the active electrode. In order to balance this flow and improve plasma generation, the fluid delivery apertures 308b on the top side may be larger in diameter, or greater in quantity than the fluid delivery apertures 308a on the under-side. In some embodiments apertures 308b may be a single elongate slot, across the width of the second exposed return electrode portion 306b. Furthermore fluid delivery channel(s) or element(s) disposed within the wand and spacer 304 may be configured to preferentially direct more flow to the upper apertures 308b than lower 308a. In some embodiments, the fluid delivery channel may be split or form two separate fluid delivery elements along a substantial portion of the wand. This may ensure a high resistance electrical pathway back into the device, forcing the current path predominantly out to the electrodes and around the outer surface of the device, instead of providing an internal conductive path electrically conductive fluid.

Figure 3B:
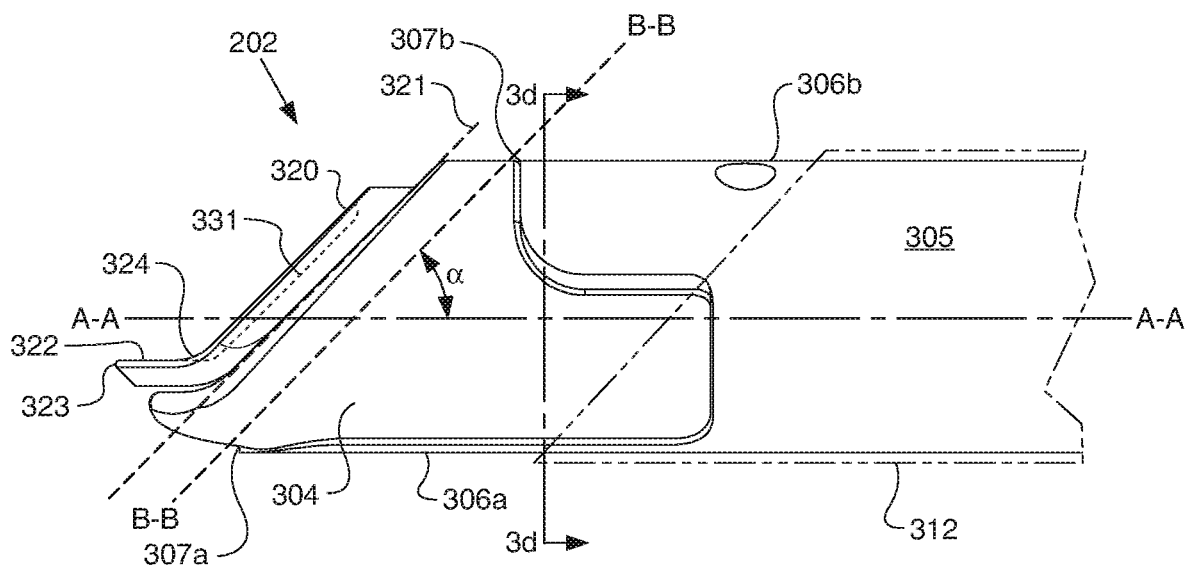

FIG. 3B show a side elevation of the first wand-tip embodiment of wand 202, showing the first and second portions of return electrode 306a and 306b extending distally from the insulating sheath 312. Both exposed portions of return electrode 306 define axially extending notches from a single shaft portion 305, the insulating shaft terminating distally from the single shaft portion 305 so as to define these two exposed portions. Insulating sheath 312 may terminate with an angled distal edge, relative to a central long axis of the distal end (A-A) of the wand distal tip, the angle defining the relative lengths and thereby surface areas of the two return electrode portions 306a and 306b. Visible also from this view is line B-B and a distal angled planar surface 321 of the spacer 304 approximately parallel to line B-B, both angled (a) between approximately 30-60 degrees and more preferably between 40-50 degrees relative to the long axis (A-A) of the wand distal tip. Line B-B defines a line approximately through distal-most edges 307 of return electrode portions 306a and 306b, so as to maintain a substantially uniform distance between the return electrode distal edges 307a and 307b and the active electrode 300. Having a substantially uniform separation may provide a more uniform tissue effect across the active electrode 300, especially when the wand is in a debulking configuration, as explained later.

The active electrode 300 defines a combination active electrode having a screen portion 320 and a blade portion 322, with a curved surface 324 there-between. The screen electrode 320 is configured to debulk a target tissue, and as shown, has an aperture 310 therethrough so as to aspirate this tissue. Screen portion 320 may also include surface asperities, such as protrusions, recesses or cavities; asperities serving to focus the electrical field intensity and thereby encourage plasma initiation and propagation and improved molecular dissociation of a target tissue. Shown here are a series of recesses, including a first horseshoe shaped recess 330 circumscribing the aspiration aperture and providing a series of elongate concentric edges for improved plasma formation around screen electrode 320, especially useful when debulking tissue. In order to further encourage plasma propagation between the outer edge surface of the active electrode 300 and the aspiration aperture 310, additional radially oriented edges 333 may be added, separating the horseshoe asperity into an increased number of segments, and may result in additional segments that appear similar to the separation between the horseshoe asperity 330 and recesses 332. Increased plasma formation may further ablate tissue adjacent the aspiration aperture 310 and may reduce clogging of said aperture 310 and the associated fluid aspiration element(s) downstream. The two smaller recesses 332 are continuous with and extend along the curve portion 324 of active electrode 300. Recesses all define bottom surfaces 331, spaced away from the top surface of the active screen electrode. Generally, during ablation mode, tissue is preferably kept in light contact with the active electrode 300 and therefore the effective surface area of the active electrode 300 during ablation is the top surface of the active electrode 300 and the recess edges. However while coagulating, the tissue preferably makes more firm contact with the active electrode 300 so that the tissue naturally conforms into the recesses (330, 332), effectively increasing the surface area of the active electrode to include the lower surfaces 331 as well as the upper surface, increasing coagulation efficiency. A larger surface area is preferable for effecting tissue coagulation.

The blade portion 322 is sized and shaped to easily access the transition between the fossa and tonsil tissue and may be curved so as to follow the anatomy. The blade portion 322 may extend distally and axially away from the spacer 304 at a sufficient length to access the underside of the tonsil. The blade portion 322 may be offset relative to a central long axis (A-A) of the wand distal end, and also disposed on an under side or first side of the wand tip closest to but laterally offset from the first portion of the return electrode 306a. Blade portion 322 may terminate with an angled or pointed tip 323 so as form an area of higher electric field intensities, preferentially forming plasma and thereby preferentially finely dissecting through tissue such as the tonsil from fossa. Stated otherwise the blade portion 322 is configured to form a cutting edge for dissection of the tonsil.

Figure 3C:
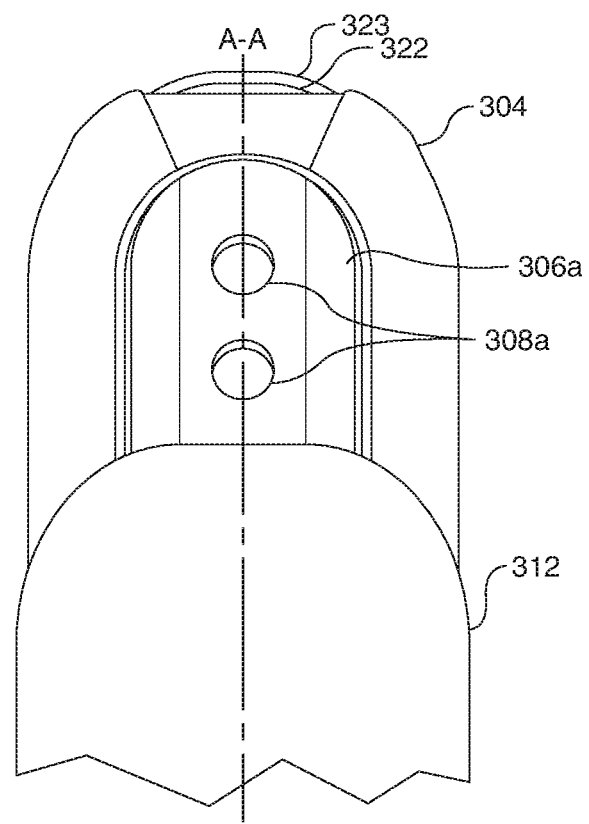

FIG. 3C shows the underside of the first wand-tip embodiment of wand 202, with first return electrode portion 306a, having a pair of axially spaced apertures 308a therethrough, the apertures 308a fluidly coupled to a fluid delivery element so that electrically conductive fluid may be delivered to the wand distal end, flow over the first return electrode portion 306a and towards the active electrode blade portion 322. Visible from this angle, the distal tip 323 of blade portion 322 also defines a curved distal edge 323, symmetrical about axis A-A so as to provide a smooth and even tissue effect around the contours of the blade portion 322 as the clinician moves the blade portion 322 between the tissues.

Figure 3D:
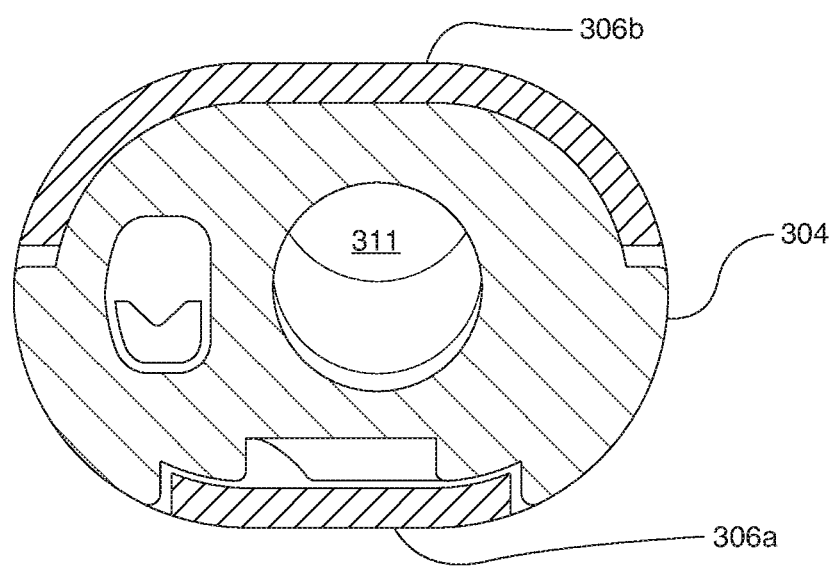
FIG. 3D shows a cross section view of a wand-tip embodiment shown in FIG. 3A-3C in accordance with at least some embodiments of the disclosure.

FIG. 3D shows a cross-section of the first wand-tip embodiment of wand 202, the position of the cross section indicated in FIG. 3B. Visible in FIG. 3D is spacer 304 with first and second exposed portion of return electrode 306a and 306b respectively. The cross-section is oblong so as to allow for an increased aspiration channel 311 through the shaft and a corresponding aperture 310 through the active electrode 300, while still allowing space for coupling of the electrode to the spacer. Visible from this view the return electrode 306 generally encircles the spacer 304; however the first exposed portion 306a encircles the spacer 304 and is limited to the under-side of the wand distal tip while the second exposed portion 306b encircles the spacer 304 further so as to encircle at least 3 sides of the spacer 304. The first exposed portion 306a is sized so that, when the wand is oriented or configured so as to influence the primary current path predominantly through the first exposed return electrode portion 306a, this exposed portion 306a behaves like a thermal electrode rather than a typical return electrode as defined, in that it now may provide some electrically-induced tissue effect. This may be achieved by either orienting the wand so as to space the second exposed portion 306b away from tissue so that the second exposed portion 306b is not in an operational relationship with tissue and/or by electrically isolating the second portion (as described later). This electrically-induced tissue effect may provide hemostasis, particularly helpful while removing tonsil tissue, where fine dissection of the tonsil is desired with some hemostasis of the tissue bed or fossa. The active electrode 300 and the first exposed portion 306a are placed closest to the target tissue and therefore set up this primary current path formed between them, more so than the screen portion 320 and second exposed portion 306b. This sets up a bipolar current path predominantly between the first exposed portion 306a and blade portion 322, that provides dissection adjacent the blade portion 322 with some concomitant hemostasis along the first exposed portion 306a. Should the first exposed portion 306a encircle a larger circumference of the wand, the resultant surface area may not provide a concomitant hemostatic tissue effect and the first exposed portion would act more like a return electrode, and thereby decreased or no tissue effect would be provided. In addition, a current path around some of the screen portion 322 may also more readily form, and thereby an unwanted tissue effect.

The second exposed portion 306b encircles the shaft to a larger extent than the first 306a as it is preferentially incorporated when the wand is used in a second orientation, so as to debulk or alternatively to coagulate tissue, across a broader surface of the active electrode 300. In the second orientation, both exposed portions of the return electrode are more equivalently parts of the current path, therefore return electrode 306 acts more as a whole (both exposed portions). In this case, the two portions of the return electrode 306 combine so as to essentially encircle a larger portion of the active electrode 320 which provides either a more uniform plasma formation and ablating tissue effect around the active electrode 300 when used to debulk adenoids, or provides a more uniform coagulating tissue effect on a larger vessel should the controller delivers a voltage configured to coagulate tissue. When coagulating tissue, such as the fossa, the screen electrode surface may be placed on tissue so that the recessed surfaces 331 are in contact with the tissue.

The portions of exposed return electrode may also differ in surface finishes, with a smoother finish on the first exposed portion 306a than the second exposed portion 306b. The inventors have found that an electro-polished surface finish is a more hydrophobic surface and has also been found to reduce tissue sticking to that surface. A rougher surface finish such as a machined or satin finish is more hydrophilic such that it may improve fluid retention on the surface, and thereby improve surface wetting, key to a uniform plasma generation. A smoother surface finish together with fluid flow on the first portion 306a therefore aids in reducing sticking during times when it acts as a thermal electrode, when sticking is more likely. Example smooth finishes range from 0.012 to 0.05 µm (micro-meters) Ra, and more hydrophilic surface finishes range from 0.8-3.2 µm Ra, where Ra is the roughness average. When placed in the second configuration where the second return electrode exposed portion 306b comes into play, the increased surface texture (rougher or satin surface) hinders the fluid from running off the surface of the second exposed portion 306b, improving surface wetting and thereby promoting a larger effective surface of return electrode around the active electrode, promoting a broader tissue effect required while debulking or alternatively when coagulating tissue.

Figure 4A:
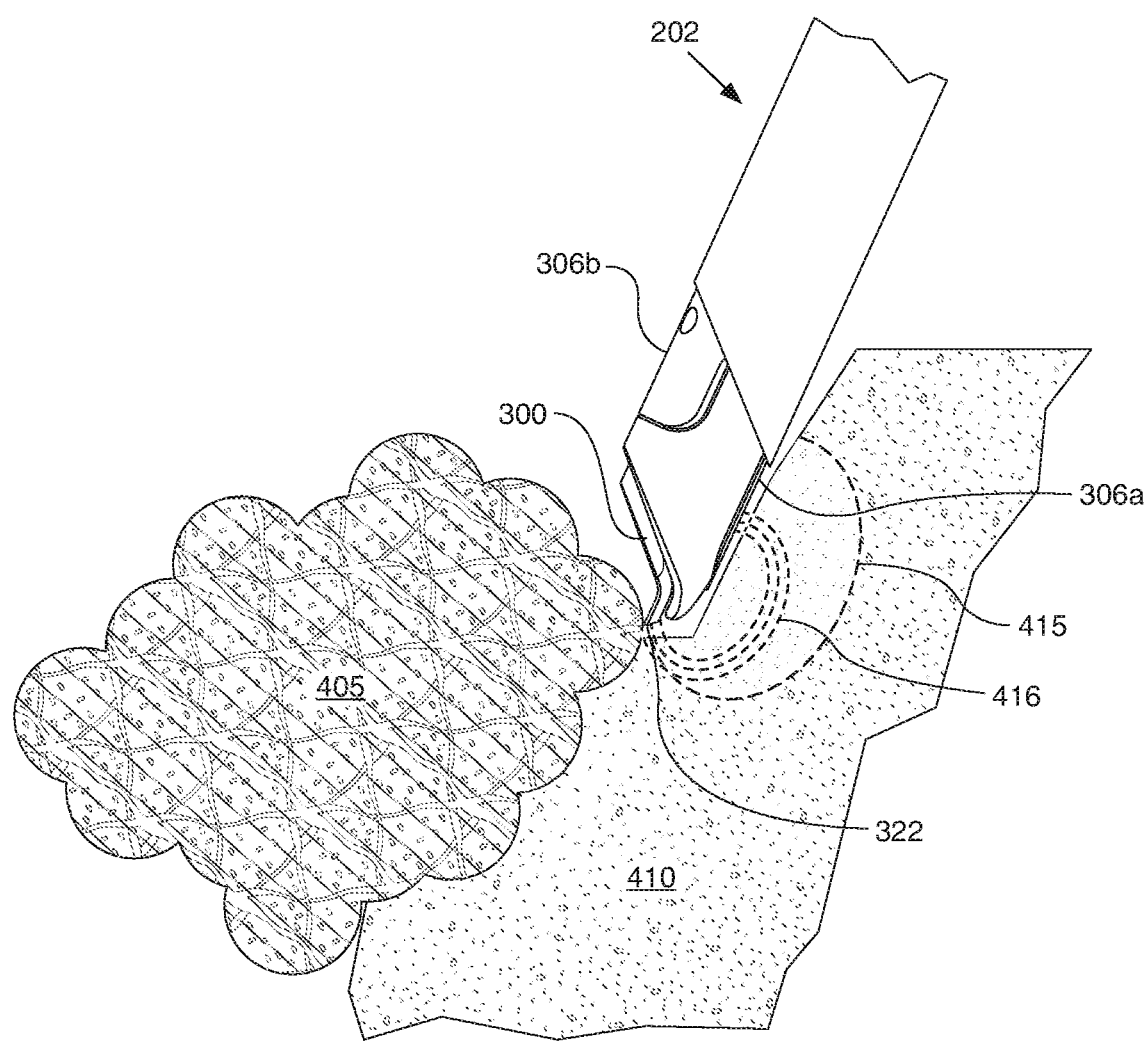
FIG. 4A shows a view of an electrosurgical wand in accordance with at least some embodiments disclosed, treating a first target tissue in a first orientation.
Figure 4B:
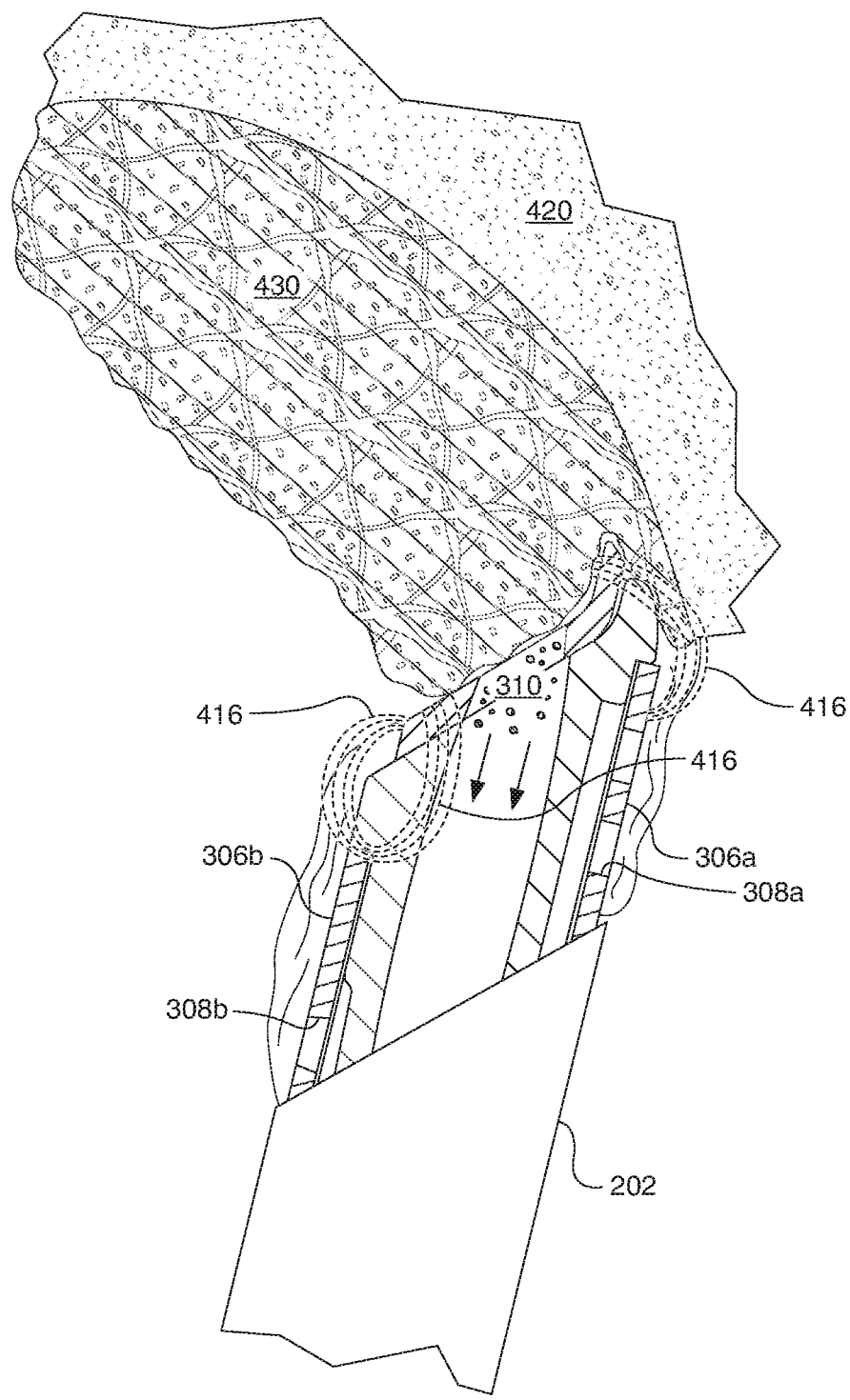
FIG. 4B shows of a view of an electrosurgical wand in accordance with at least some embodiments disclosed, treating a second target tissue in a second orientation.

FIGS. 4A and 4B show two orientations relative to tissues, and a method of use. In the first orientation shown in FIG. 4A, the wand may be positioned so as to finely dissect tonsils 405 or disconnect the tonsils 405 from the fossa or tissue bed 410 using primarily the blade portion 322. As explained earlier, in this first orientation first return electrode exposed portion 306a is primarily in contact with and parallel to the tissue bed 410, partly due to the bend 103 (shown in previous figures) and therefore the first exposed portion 306a is part of the primary current flow path 416 with respect to the active electrode 300. The second return electrode exposed portion 306b is spaced away from tissue and minimal current may flow between active electrodes 300 and second portion 306b. (Some current may flow as a result of the electrically conductive fluid flow from aperture 308b, but the second exposed portion is not in an operational relationship with the tissue.) As explained earlier, this temporarily converts the first exposed portion 306a to act as a thermal electrode, providing some concomitant heating and hemostasis 415 of the tissue bed 410 in use in the first orientation. In alternative embodiments the two exposed return electrode portions 306a and 306b may be formed as two electrically isolated elements, individually coupled to a controller and multiplexed accordingly; however this embodiment may require additional controls and multiplexing in the controller and may add costs to both the wand and controller generally.

While treating tonsils, the wand 202 may be temporarily rotated (not shown), and operated in a coagulation mode so as to treat larger vessels adjacent the tonsil. These vessels are typically a part of the fossa, or connecting the fossa to the tonsil. In this orientation a substantial portion of active electrode screen portion 320 is placed in contact with tissue bed 410 including the lower surfaces 331 of recesses. Both exposed portions of the return electrode 306a and 306b are more equivalently adjacent the fossa 415. In this coagulating configuration, electrically conductive fluid may flow from apertures 308a and 308b and help bridge a current path 416 from both exposed return electrode portions 306a and 306b around and over the active electrode 300 towards the aspiration aperture 310. Together with an RF output configured to coagulate tissue, a coagulating tissue effect across a broader surface of the active electrode 300 to seal vessels is then achieved, before possibly returning to the first orientation and continuing to dissect the tonsil tissue. In addition, the controller may alter the fluid flow rate when in coagulation mode; and may reduce the fluid flow rate relative to the dissecting or fine ablation mode.

In a second orientation, the wand is reoriented as shown in FIG. 4B and operated in a debulking or fast ablation mode. In this orientation, a substantial portion of active electrode screen portion 320 is adjacent adenoid tissue 430, and both exposed portions of the return electrode 306a and 306b are more equivalently spaced from the adenoid tissue 430. In this second configuration, electrically conductive fluid flows from apertures 308a and 308b around and over the active electrode 300 towards the aspiration aperture 310 to form a current path 416 from both exposed return electrode portions 306a and 306b. Blade portion 322 and curve 324 are also configured to scoop adenoid tissue 430 towards the screen electrode 320. This allows a broader tissue effect across the active electrode 300 so as to debulk or molecularly dissociate broader portions of adenoid tissue 430 and remove the adenoid tissue 430 from the tissue bed 420 in a debulking fashion. In this orientation, the bend 103 may be altered or a second bend along the wand shaft 106 may be added by the clinician so as to better access the adenoid tissue 430. In addition, the controller may adjust the fluid flow delivery rate in this second orientation, so as to increase the fluid flow rate relative to the dissecting mode, this increased fluid delivery rate improving the flow of by-products through the aspiration aperture 310, improving tissue debulking.

Second Embodiment

Figure 5A:
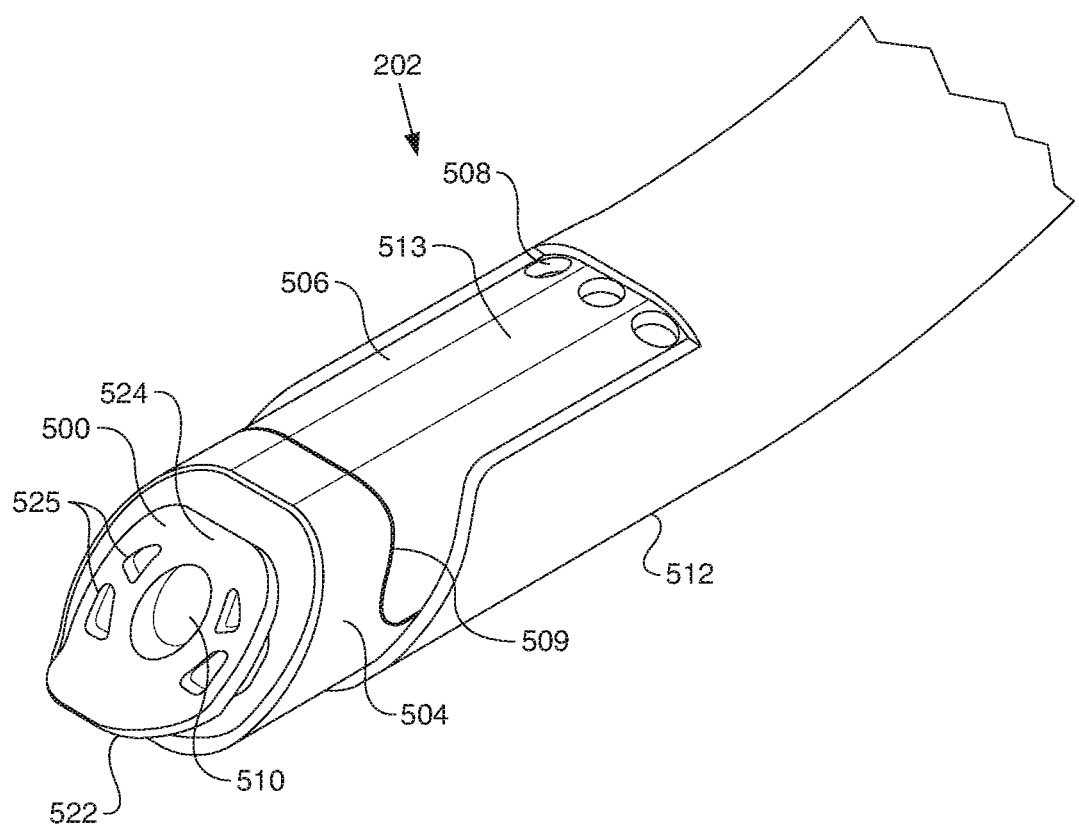
FIGS. 5A and 5B show a perspective view and a side view respectively of a second wand-tip embodiment in accordance with at least some embodiments of the disclosure.
Figure 5B:
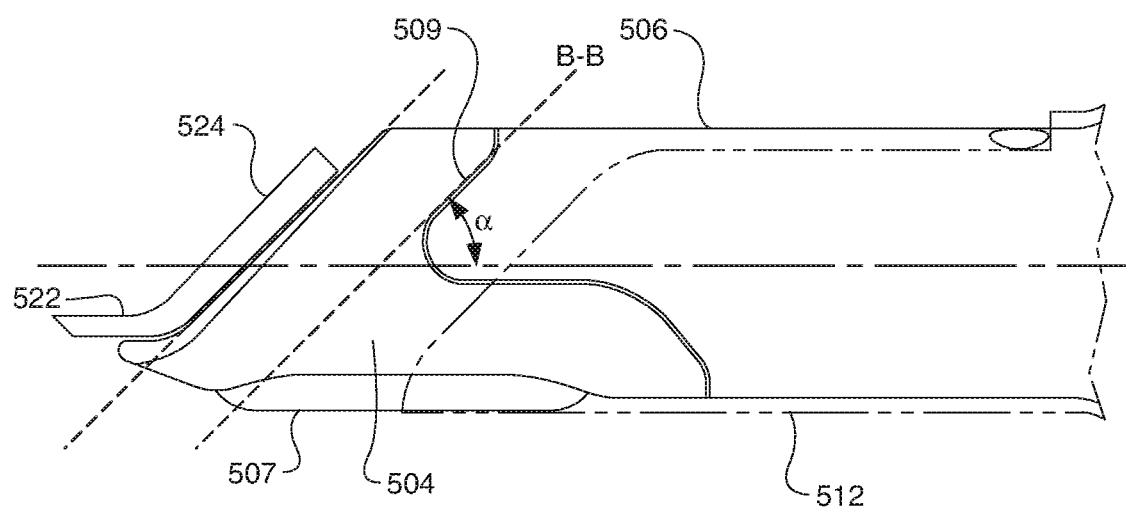

FIGS. 5A and 5B show a perspective view and a side view respectively of a wand 202 with a second wand-tip embodiment in accordance with example systems. This second embodiment includes many similar elements to the first wand-tip embodiment, and may be used to treat a variety of tissues such as the tonsils and adenoids in a similar manner as explained earlier. Similar elements include the combination active electrode 500 having a blade portion 522 and screen portion 524 disposed on a spacer 504, and return electrode 506 with fluid delivery apertures 508. Screen portion 524 shows alternative surface asperities 525 that are shown as pockets or recesses disposed circumferentially around the aspiration aperture 510; the asperities 525 forming edges on the screen electrode planar surface that focus the electrical field generation, and thereby encouraging plasma initiation. These asperities 525 have been found to improve debulking a target tissue when placing the screen electrode planar surface adjacent a target tissue. Visible also on FIG. 5A is an upper return electrode 506 with fluid delivery apertures 508 on a proximal end thereof and an elongate channel 513 formed by edges of insulative sheath 512, such that fluid flowing from apertures 508 will flow over an elongate portion of upper return electrode 506, towards active electrode 500. Shown also in this embodiment is an alternative embodiment for a distal edge 509 of upper return electrode 506, as it encircles the shaft. The distal edge 509 extends further at an angle α approximately parallel to the screen electrode portion 524 and line B-B, as described in pervious embodiments. This maintains a longer edge length at a uniform spacing between the return and active electrodes, relative to the distal edges shown in the first wand-tip embodiment, and thereby has shown to more consistently treat tissue as desired when the upper return electrode portion 506 is part of the current path.

Visible in FIG. 5B is a lower electrode 507 and spacer 504 which completely surrounds lower electrode 507 disposed on the opposite side of the wand from the upper return electrode 506. Lower electrode 507 may also have a plurality of fluid flow apertures there-through, similar to the first exposed return electrode described in the first wand-tip embodiment. Unlike the first wand-tip embodiment, upper return electrode 506 is electrically isolated from the lower electrode 507, so that lower electrode 507 is not necessarily an exposed portion of a shaft. The upper return electrode 506 may therefore be independently electrically coupled to the controller (described later) or electrically coupled with the lower electrode 507, depending on the desired tissue effect and target tissue. Stated otherwise, in the first orientation described in FIG. 4A, the lower electrode 507 may be electrically coupled to the return terminal of the controller, while the upper return electrode 506 may be electrically isolated; while in the second orientation described in FIG. 4B, both upper and lower electrodes 506 and 507 may be electrically coupled to the return terminal. Second wand-tip embodiment may be bipolar or has an opportunity to be coupled in a tripolar mode, described later.

Third Embodiment

Figure 6A:
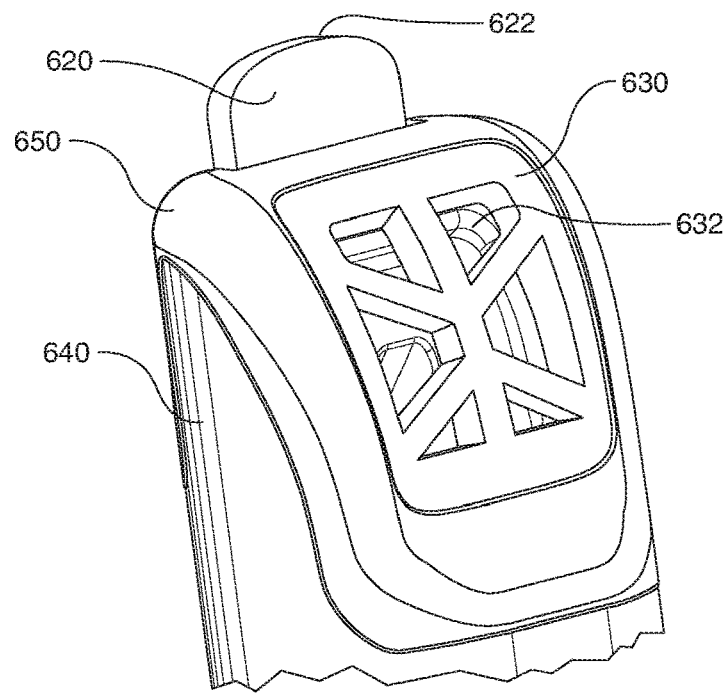
FIGS. 6A and 6B show a front perspective view and a rear perspective view of a third wand-tip embodiment respectively in accordance with at least some embodiments of the disclosure.
Figure 6B:
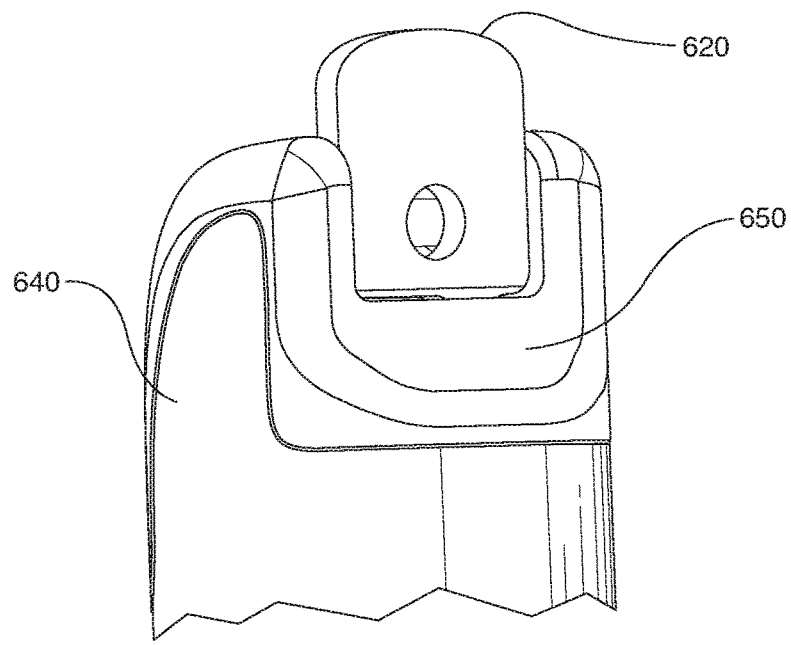

FIGS. 6A and 6B shows a front perspective view and a rear perspective view of a third wand-tip embodiment respectively. In this embodiment, three distinct electrodes are formed, including a first electrode 620 configured with a distal blade portion 622 for finely dissecting tissue from a tissue bed such as tonsils from the fossa. Similar to the second embodiment, the second electrode 630 and third electrode 640 may be independently electrically coupled to the controller and all electrodes may be isolated from each other to provide the opportunity for tripolar activation wherein a plurality of combinations of electrodes may be activated to achieve a variety of tissue effects. Similar to previously described wand-tip embodiments, a spacer 650, comprising electrically insulating material as described earlier may support while electrically isolating the three electrodes. For example while removing the tonsil, second electrode 630 may also be simultaneously coupled as an active electrode, to either the same active terminal as the blade electrode 620 or to a different active terminal and placed closest to the tissue bed, while third electrode 640 may be coupled as a return electrode, so that the second electrode may provide concomitant hemostasis to the tissue bed during dissection. The second electrode 630 may have a broader exposed surface area than the first active (blade) electrode 620. The second electrode may be a screen style electrode as shown. The second electrode may be disposed on the opposite side of the distal end from the active (blade) electrode 620, such that the second electrode has a planar exposed surface, and the second electrode may have a curve so as to improve proximity to the fossa tissue and follow the shape of the local anatomy. Apertures 632 may extend through second electrode 630 providing a fluid flow path to a suction or aspiration lumen. Apertures 632 may have sharp edges to promote plasma formation. The second electrode may also have a 3D shape, tapering through its thickness, especially through the apertures 632 so as to direct the fluid flow path as fluid is aspirated through the apertures 632. At yet still other times, the second electrode may be coupled as a return electrode.

Similar to previously described return electrodes, third electrode 640 may encircle at least a portion of the shaft with a distal end that is shaped so as to maintain a somewhat consistent distance between the proximal portion of the active (blade) electrode 620 and also a consistent distance between a proximal portion of the secondary electrode along some portions. The third electrode 640 may be an active or a return electrode.

In an adenoid mode of operation the second electrode 630 is the active electrode, with the blade electrode potentially electrically floated. While debulking adenoids the second electrode 630 may be supplied with energy sufficient to form plasma and rapidly remove the adenoid tissue. The energy to the second or screen electrode 630 may be pulsed as discussed later to implement concomitant cutting and coagulation. Disassociated tissue may be removed through the plurality of apertures 632 through the second electrode 630.

Fourth Embodiment

Figure 7A:
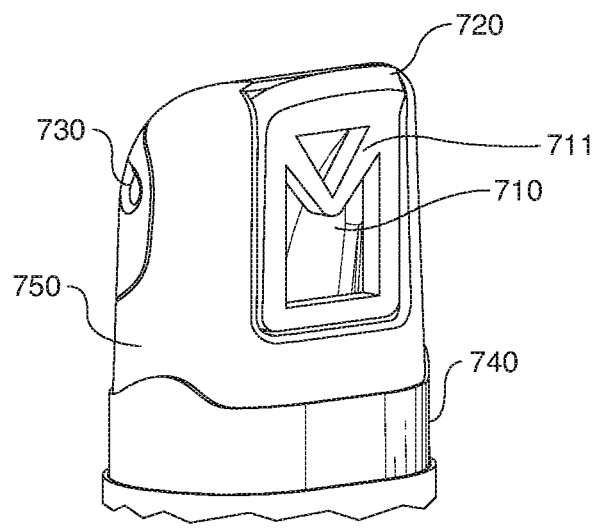
FIGS. 7A and 7B show a front and rear perspective view respectively of the distal tip of a fourth wand-tip embodiment in accordance with at least some embodiments of the disclosure.
Figure 7B:
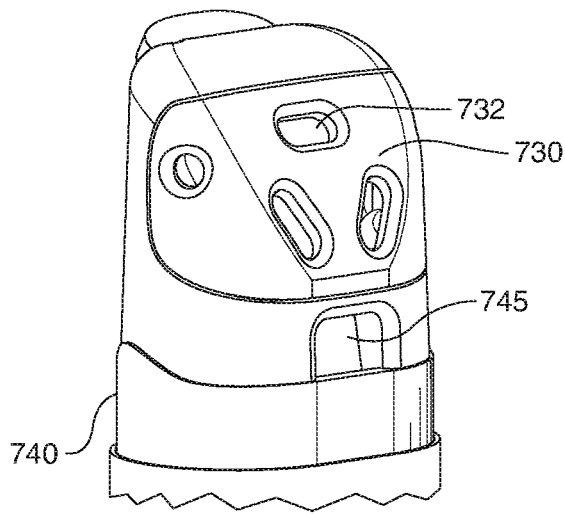

FIGS. 7A and 7B shows a front and rear perspective view respectively of the distal tip of a fourth wand-tip embodiment. Similar to some previously embodiments, this wand-tip embodiment may be coupled as a tripolar wand, with independently coupled electrodes as either an active or return electrode, depending on the desired tissue effect; for example to provide precise tissue cutting or ablation at an ablation electrode and concomitant hemostasis from at least one of the other electrode (return or thermal). Similar to the previous embodiment, the primary electrode for fine dissection 720 has a distal tip that extends away from spacer 750 with a tip shape configured to provide a cutting tissue effect (sharper more pointed end). The primary electrode 720 is shown with an aperture 710 for aspirating plasma by-products and fluid away from the area. The primary ablation electrode also has a V-shaped bridge 711 to further ablate tissue before aspiration.

The designated return electrode 730 may have a larger surface area than the ablation electrode 720 and is located on the opposite side of the wand distal end from the ablation electrode 720 so as to be part of the electrode circuit responsible for coagulation of the fossa during the removal of tonsils. The return electrode 730 may have apertures 732 or holes to draw fluid there through. Fluid and plasma by-products may be aspirated through the return electrode 730, or electrically conductive fluid may be delivered through these holes.

The thermal electrode 740 shown in both FIGS. 7A and 7B may form part of the electrode circuit with the return electrode 730 to provide hemostasis of the fossa. The thermal electrode 740 and return electrode 730 may be interchangeable, providing slightly different electrical fields around the wand distal tip and thereby a blended tissue effect over the surface of the wand-tip, ranging from an ablating or cutting tissue effect in a first location near a first electrode (720) with a simultaneous heating or coagulating tissue effect at a second location near a second electrode (720 or 730). Similar to the previous embodiment, the thermal electrode 740 encircles at least a portion of the wand shaft. A fluid delivery aperture 745 may also be disposed between the return electrode 730 and thermal electrode 740, on the same side as the return electrode 730.

Fifth Embodiment

Figure 8:
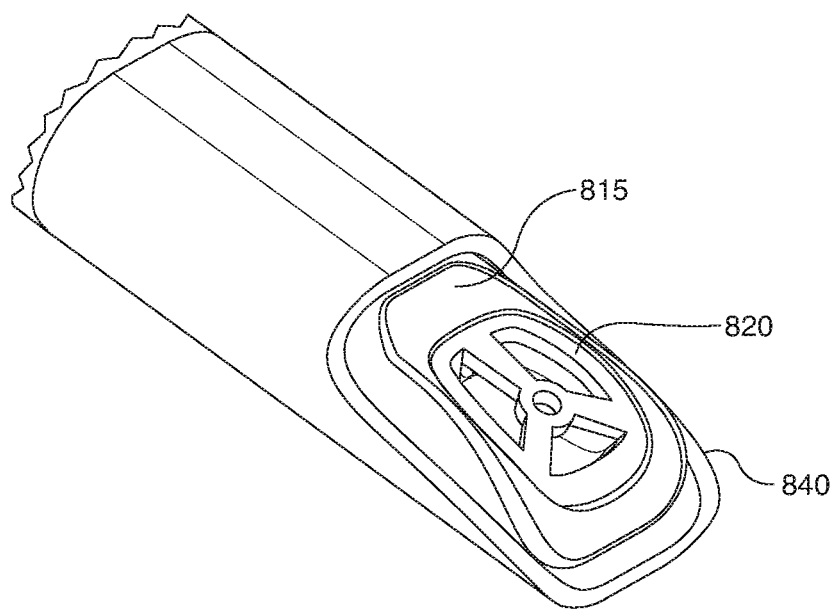
FIG. 8 shows a perspective view of the distal tip of a fifth wand-tip embodiment in accordance with at least some embodiments of the disclosure.

FIG. 8 shows a perspective view of the distal end of a fifth wand-tip embodiment in accordance with at least some embodiments. In particular, the fifth ENT wand-tip embodiment is a bipolar wand-tip arrangement. The example wand tip of FIG. 8 comprises an active screen-type electrode 820 on an upper-side surface of the wand. The active screen-type electrode 820 resides over an aspiration lumen through which fluids and tissue fragments may be aspirated. The active screen-type electrode 820 is surrounding or circumscribed by the return electrode 840 that includes a surface opposite the active electrode 820, and moreover the return electrode 840 in the example embodiments extends beyond the distal tip of the support member 815 that holds the active screen-type electrode 820.

The embodiment is targeted for adenoids only and has two electrodes only. The active electrode 820 is configured to debulk tissue, by molecular dissociation, as described earlier and is disposed at an angle and location that is configured for improved access to adenoid tissue. The return electrode 840 extends around and further than the active electrode 820 so as to improve the contact between the return electrode 840 and tissue and fluid adjacent the adenoid, as the wand is moved around and thereby improving the consistency of the electrode circuit that includes plasma. This is envisioned to improve the overall tissue effect while debulking the adenoids.

Controller

Figure 9:
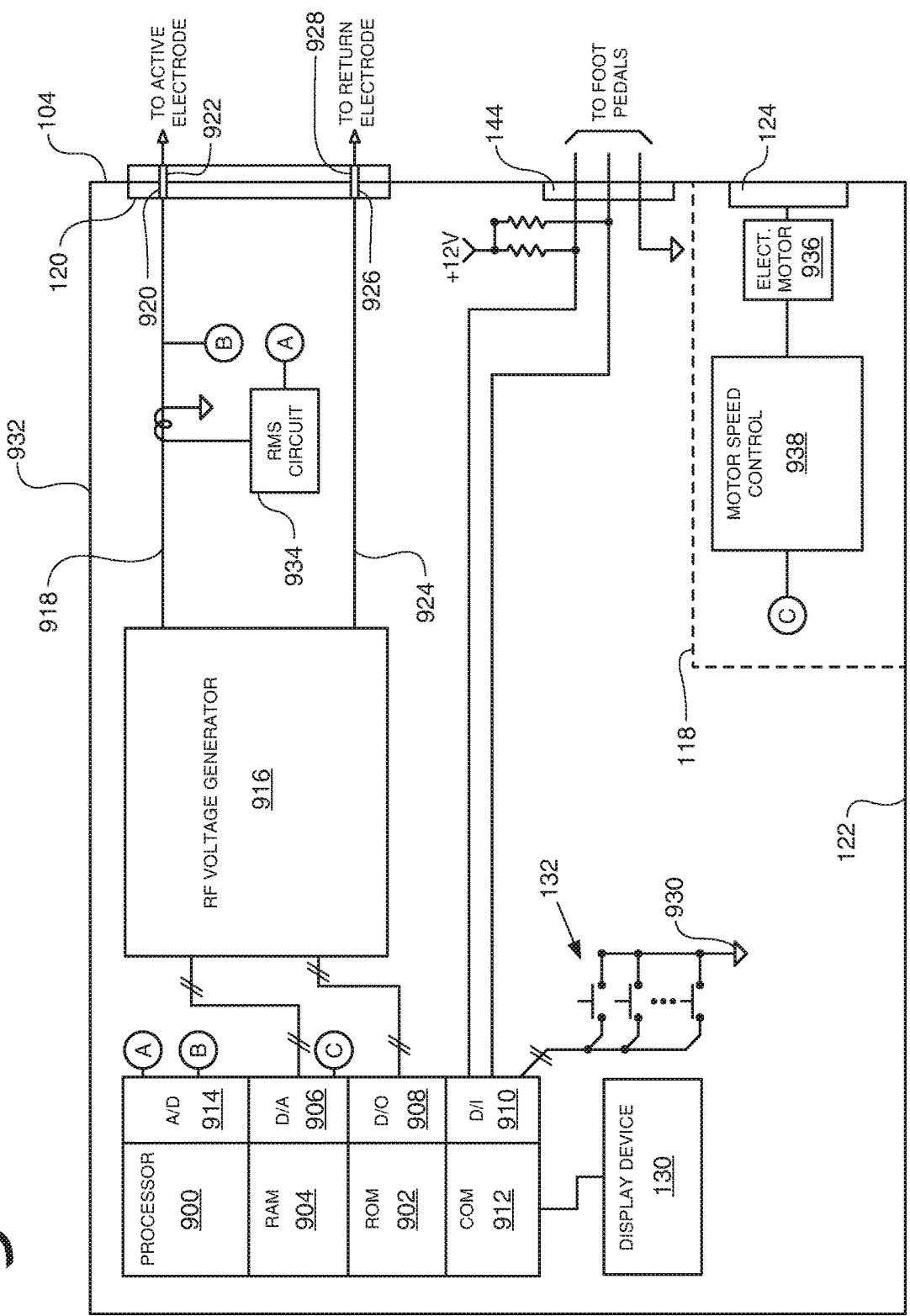
FIG. 9 shows a schematic of a first controller system in accordance with at least some embodiments.

FIG. 9 shows an electrical block diagram of controller 104 in accordance with at least some embodiments. In particular, the controller 104 comprises a processor 900. The processor 900 may be a microcontroller, and therefore the microcontroller may be integral with read-only memory (ROM) 902, random access memory (RAM) 904, flash or other non-volatile programmable memory, digital-to-analog converter (D/A) 906, analog-to-digital converter (A/D) 914, digital outputs (D/O) 908, and digital inputs (D/I) 910. The processor 900 may further provide one or more externally available peripheral busses (e.g., I2C, USB). The processor 900 may further be integral with communication logic 912 (e.g., UARTs, Ethernet enabled ports) to enable the processor 900 to communicate with external devices, as well as internal devices, such as display device 130. Although in some embodiments the processor 900 may be implemented in the form of a microcontroller, in other embodiments the processor 900 may be implemented as a standalone central processing unit in combination with individual RAM, ROM, communication, A/D, D/A, DO, DI devices, and communication hardware for communication to peripheral components. In some example systems, the processor 900 and related functionality are implemented as a MK60 series microcontroller available from Freescale Semiconductor of Austin, Tex.; however, other microcontrollers may be equivalently used.

ROM 902 (or possibly a flash memory) stores instructions executable by the processor 900. In particular, the ROM 902 may comprise a software program that, when executed, causes the processor to sum, over various time windows, energy delivery and when needed temporarily cease or "pulse" the energy provided to ensure the rate of energy delivery does not exceed predetermined thresholds (discussed more below). The RAM 904 may be the working memory for the processor 900, where data may be temporarily stored and from which instructions may be executed. Processor 900 couples to other devices within the controller 104 by way of the digital-to-analog converter 906 (e.g., in some embodiment the RF voltage generator 916), digital outputs 908 (e.g., in some embodiment the RF voltage generator 916), digital inputs 910 (e.g., interface devices such as push button switches 132 or foot pedal assembly 134 (FIG. 1)), and communication device 912 (e.g., display device 130).

Voltage generator 916 generates an alternating current (AC) voltage signal that is coupled to active electrode(s) (e.g., active electrode 200) of the example wand. In some embodiments, the voltage generator defines an active terminal 918 which couples to electrical pin 920 in the controller connector 120, electrical pin 922 in the wand connector 114, and ultimately to the active electrode(s). Likewise, the voltage generator defines a return terminal 924 which couples to electrical pin 926 in the controller connector 120, electrical pin 928 in the wand connector 114, and ultimately to the return electrode(s). Additional active terminals and/or return terminals may be used. The active terminal 918 is the terminal upon which the voltages and electrical currents are induced by the voltage generator 916, and the return terminal 924 provides a return path for electrical currents. It would be possible for the return terminal 924 to provide a common or ground being the same as the common or ground within the balance of the controller 104 (e.g., the common 930 used on push-buttons 132), but in other embodiments the voltage generator 916 may be electrically "floated" from the balance of the controller 104, and thus the return terminal 924, when measured with respect to the common or earth ground (e.g., common 930) may show a voltage; however, an electrically floated voltage generator 916 and thus the potential for voltage readings on the return terminals 924 relative to earth ground does not negate the return terminal status of the terminal 924 relative to the active terminal 918.

The AC voltage signal generated and applied between the active terminal 918 and return terminal 924 by the voltage generator 916 is RF energy that, in some embodiments, has a frequency of between about 5 kilo-Hertz (kHz) and 20 Mega-Hertz (MHz), in some cases being between about 30 kHz and 2.5 MHz, in other cases being between about 50 kHz and 500 kHz, often less than 350 kHz, and often between about 100 kHz and 200 kHz. In some applications, a frequency of about 100 kHz is useful because target tissue impedance is greater at 100 kHz.

The RMS (root mean square) voltage generated by the voltage generator 916 may be in the range from about 5 Volts (V) to 1800 V, in some cases in the range from about 10 V to 500 V, often between about 10 V to 400 V depending on the mode of ablation and active electrode size. The peak-to-peak voltage generated by the voltage generator 916 for ablation in some embodiments is a square waveform in the range of 10 V to 2000 V, in some cases in the range of 100 V to 1800 V, in other cases in the range of about 28 V to 1200 V, and often in the range of about 100 V to 740 V peak-to-peak.

The voltage and current generated by the voltage generator 916 may be delivered as a square wave voltage signal or sine wave voltage with a sufficiently high frequency (e.g., on the order of 5 kHz to 20 MHz) such that the voltage is effectively applied continuously as compared with, e.g., lasers claiming small depths of necrosis, which are pulsed about 10 Hz to 20 Hz). In addition, the duty cycle of a square wave voltage produced by the voltage generator 916 is on the order of about 50% for some embodiments (e.g., half the time as a positive voltage square signal, and half the time as a negative voltage square signal) as compared with pulsed lasers which may have a duty cycle of about 0.0001%. Although square waves are generated and provided in some embodiments, the AC voltage signal is modifiable to include such features as voltage spikes in the leading or trailing edges of each half-cycle, or the AC voltage signal is modifiable to take particular shapes (e.g., sinusoidal, triangular).

The voltage generator 916 delivers average power levels ranging from several milliwatts to hundreds of watts per electrode, depending on the mode of operation and state of the plasma proximate to the active electrode(s). The voltage generator 916 in combination with the processor 900 are configured to set a constant root mean square (RMS) voltage output from the voltage generator 916 based on the mode of operation selected by the surgeon (e.g., one or more ablation modes, coagulation mode). A description of various voltage generators 916 can be found in commonly assigned U.S. Pat. Nos. 6,142,992 and 6,235,020, the complete disclosure of both patents are incorporated herein by reference for all purposes. Reference is also made to commonly assigned U.S. Pat. No. 8,257,350, titled "METHOD AND SYSTEM OF AN ELECTROSURGICAL CONTROLLER WITH WAVE-SHAPING", the complete disclosure of which is incorporated herein by reference as if reproduced in full below.

In some embodiments, the voltage generator 916 may be controlled by a program executing on the processor 900 by way of digital-to-analog converter 906. For example, the processor 900 may control the output voltages by providing one or more variable voltages to the voltage generator 916, where the voltages provided by the digital-to-analog converter 906 are proportional to the voltages to be generated by the voltage generator 916. In other embodiments, the processor 900 may communicate with the voltage generator by way of one or more digital output signals from the digital output converter 908, or by way of packet-based communications using the communication device 912 (the communication-based embodiments not specifically shown so as not to unduly complicate FIG. 9).

Still referring to FIG. 9, in some embodiment the controller 104 further comprises a mechanism to sense the electrical current provided to the active electrode. In the illustrative case of FIG. 9, sensing current provided to the active electrode may be by way of a current sense transformer 932. In particular, current sense transformer 932 may have a conductor of the active terminal 918 threaded through the transformer such that the active terminal 918 becomes a single turn primary. Current flow in the single turn primary induces corresponding voltages and/or currents in the secondary. Thus, the illustrative current sense transformer 932 is coupled to the analog-to-digital converter 914. In some cases, the current sense transformer may couple to the analog-to-digital converter 914 through amplification circuits, protection circuits, and/or circuits to convert the sensed values to RMS. In particular, in the example system of FIG. 9 the current sense transformer couples to an RMS circuit 934. RMS circuit 934 is an integrated circuit device that takes the indication of current from the current sense transformer 932, calculates a RMS value over any suitable period of time (in some example systems, over a 10 millisecond rolling window), and provides the RMS current values to the processor 900 through the analog-to-digital converter 914 (shown by bubble A). Other communicative couplings between the RMS circuit 934 and the processor 900 are contemplated (e.g., serial communication over an I2C or USB pathway, Ethernet communication). The current sense transformer 932 is merely illustrative of any suitable mechanism to sense the current supplied to the active electrode, and other systems are possible. For example, a small resistor (e.g., 1 Ohm, 0.1 Ohm) may be placed in series with the active terminal 918, and the voltage drop induced across the resistor used as an indication of the electrical current. Given that the voltage generator 916 is electrically floated, the mechanism to sense current is not limited to the just the active terminal 918. Thus, in yet still further embodiments, the mechanism to sense current may be implemented with respect to the return terminal 924. For example, illustrative current sense transformer 932 may be implemented on a conductor associated with the return terminal 924.

Still referring to FIG. 9, controller 104 in accordance with example embodiments further comprises the peristaltic pump 118. The peristaltic pump 118 may reside at least partially within the enclosure 122. The peristaltic pump comprises the rotor 124 mechanically coupled to a shaft of the electric motor 536. In some cases, and as illustrated, the rotor of the electric motor may couple directly to the rotor 124, but in other cases various gears, pulleys, and/or belts may reside between the electric motor 936 and the rotor 124. The electric motor 936 may take any suitable form, such as an AC motor, a DC motor, and/or a stepper-motor. To control speed of the shaft of the electric motor 936, and thus to control speed of the rotor 124 (and the volume flow rate at the wand), the electric motor 936 may be coupled to a motor speed control circuit 938. In the illustrative case of an AC motor, the motor speed control circuit 938 may control the voltage and frequency applied to the electric motor 936. In the case of a DC motor, the motor speed control circuit 938 may control the DC voltage applied to the electric motor 936. In the case of a stepper-motor, the motor speed control circuit 938 may control the current flowing to the poles of the motor, but the stepper-motor may have a sufficient number of poles, or is controlled in such a way, that the rotor 124 moves smoothly. Stated otherwise, the rotor 124 moves smoothly due to the high number of steps per turn. The processor 900 couples to the motor speed control circuit 936, such as by way of the digital-to-analog converter 906 (as shown by bubble C).

Figure 10:
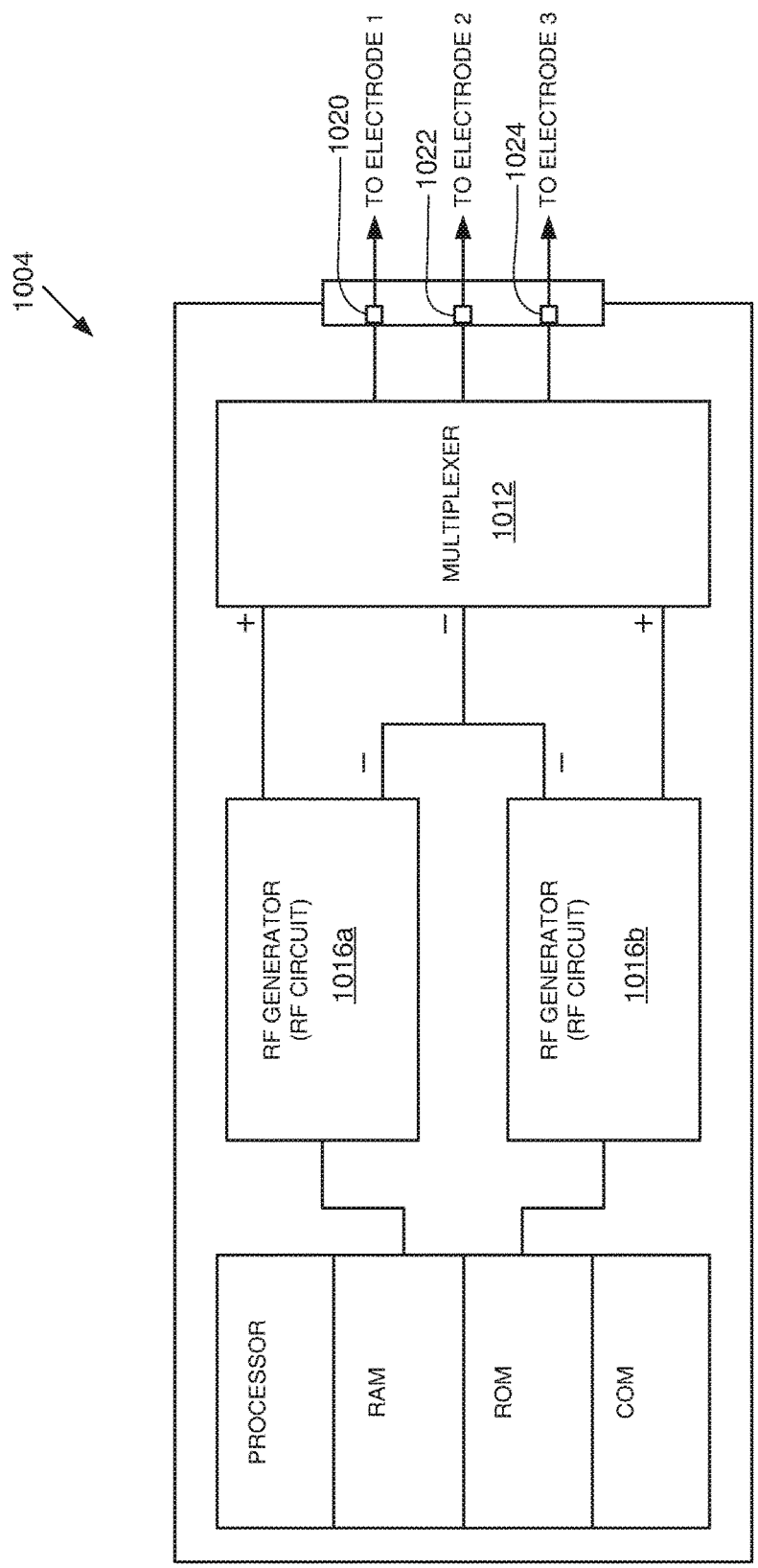
FIG. 10 shows a schematic of a second controller system in accordance with at least some embodiments.

FIG. 10 shows a block diagram of a controller 1004 in accordance with a second embodiment. In particular, second embodiment is similar to controller embodiment described earlier, with the exception of an additional independent RF generator in communication with the controller, so as to define a first voltage generator 1016a and a second voltage generator 1016b that may operate simultaneously. Each RF generator is configured to deliver a selectable and variable range of RF outputs to a distal end of an electrosurgical wand. Using these two RF generators together with multiplexer 1012 and software control, along with a wand having at least two electrodes, a great variety of independently controlled RF outputs can be provided to vary the tissue effect at and between each electrode.

The RF output variables that may be independently modified by the controller 1004 may include: regulation modes (e.g., voltage regulated, power regulated, current regulated); peak or root-mean-square (RMS) voltages (e.g., selected to either develop varying intensities of electrical field and therefore varying energy levels of electrons within the plasma, or lower voltages sufficient to coagulate tissue); pulsing rates and duty cycles (e.g., interrupting the output or modulating the output may blend cutting and coagulation at a single electrode and may also reduce tissue sticking), which can also work on a regular bipolar wand; and output waveforms (e.g., sine waveform, square waveform).

The RF controller 1004 with at least two independent RF generators 1016a and 1016b are selectively coupled to at least two pins of a controller connector, and oftentimes connected to three pins (1020, 1022 and 1024) and potentially more. The pins (1020, 1022 and 1024) may be electrically coupled to at least one electrode on an electrosurgical wand. The return terminals may be permanently electrically coupled to each other and may be one input to the multiplexer.

Selection may occur using a combination of software control in communication with a multiplexer 1012. Each RF generator 1016a and 1016b is configured to selectively and potentially independently supply RF energy to electrodes on a wand. RF energy may be delivered from each independent circuit at differing potentials setting up a range of electrical field intensities at and around each electrode, as well as different waveforms (e.g., square waveforms for plasma ablation and sine waveforms for coagulation), differing frequencies, different pulsing levels or duty cycles and also different regulation modes (e.g., current regulated, voltage regulated, or power regulated). Output voltages may be high enough to develop high electric field intensities sufficient to form plasma at the electrode, or lower so as to desiccate or coagulate tissue. Pulsing or modulating the RF voltage may interrupt or reduce any vapor layer formed, so that some hemostasis occurs during the thermal phase of the cycle before a vapor layer is formed and subsequently the plasma and thereby the cutting tissue effect. Pulsing may also help reduce the sticking of tissue to the wand electrode.

Output energy from each RF generator may be delivered simultaneously with varying levels (voltages, waveforms, pulsing) relative to each other so as to supply a blended effect of both cutting and hemostasis. For example, an output configured to initiate plasma may be supplied to a first electrode from a first RF generator at the same time as an output configured to coagulate tissue is supplied from a second RF generator to a second electrode so as to provide a multi-polar blended tissue effect at the distal end of the wand. A third terminal from either or both RF generators may be selectively or fixedly assigned as a return. More specifically as an example, looking back at the wand tip embodiment in FIG. 6, while dissecting the tonsils, an output configured to ablate tissue may be supplied to the active electrode 620 from a first RF generator 1016*a* and may be a pulsed output, at the same time as an output configured to coagulate tissue being supplied from a second RF generator 1016*b* to electrode 630. Electrode 640 may be coupled to the return terminal of either or both the RF generators 1016*a* or 1016*b*. This example output would set up a multipolar blended tissue effect along the length of the wand distal tip with a cutting tissue effect at the distal end blending to a more hemostatic tissue effect towards the more proximal end of screen electrode 630. Advantageously one RF generator has the ability to deliver RF energy that is voltage controlled, with square waveform at a relative high voltage that is preferable for ablation, while the second RF generator has the ability to deliver RF energy that may be power regulated with a sine waveform at a relatively lower voltage, that may be more preferable for coagulation. How the voltages/potentials interact between all the electrodes including the return electrode also alters the tissue effect. By altering the relative levels of voltage or energy output from each RF generator, or by pulsing at least one of these output circuits (described later), a blend of cutting and levels of hemostasis may be achieved both at each individual electrode as well as between the electrodes along the wand distal end in general, as the electrical fields interact. The blended cut may be selectively altered by the user on a sliding scale (e.g., to supply increased or reduced cutting relative to hemostasis). The controller 1004 containing the RF generators (1016*a* and 1016*b*) may enable a user to independently select levels of cutting and coagulation at each electrode, or may also enable the user to select modes (described later) that may be programmed with preset levels of outputs to pre-set electrodes. Alternatively, the user may choose a tissue effect mode or tissue type mode (e.g., debulking mode. or adenoid mode) that automatically selects a recommended output for each electrode. These preset levels may also be wand dependent.

The controller 1004 may also control the timing of each of the independent RF generators (1016*a* and 1016*b*) so that energy is delivered so as to overlap for some period of time or alternate with each other. There may also be a pre-set time delay between activating a first active electrode pair and a second active electrode pair, for example to initiate plasma at a first electrode or electrode array of a wand for a period of time, for a few seconds before activating a coagulating output between the second electrode.

The independent RF generators (1016*a* and 1016*b*) may be both software controlled with some relays or other switching system (multiplexer) included in the system to selectively couple the RF generators with the output pins in the connector. The controller program and memory may assign a range of outputs that can include "pure cutting," "low temperature coagulation," or cutting with a variable level of hemostasis or varying blends between cutting and hemostasis. For example, pure cutting mode may be achieved using voltage regulated output, with a uniform square waveform at a constant rate to a first cutting electrode. A level of cutting with some hemostasis may be achieved by adjusting or periodically interrupting the output described above to the first cutting electrode only. A blend including cutting with an even more hemostasis that stretches across a broader area of the wand tip may be achieved by further adjusting the interruption rate at the cutting electrode and/or activating a second electrode with RF delivery configured for hemostasis or coagulation (e.g at a second lower voltage than the voltage supplied to the cutting electrode, and possibly in a power control mode). Having independent RF generators enables a variety of RF outputs that are selectively coupled to varying electrodes on a wand so as to offer a broad range of tissue effects at each electrode (e.g., selected based on the procedure and tissue type).

Pulsing or Modulated Output

Figure 11A:
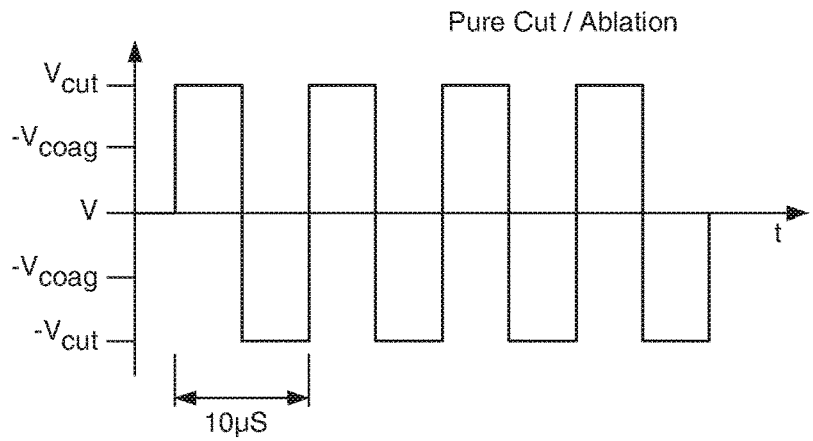
FIG. 11A-C show a representation of varying energy outputs of a controller system in accordance with at least some embodiments.
Figure 11B:
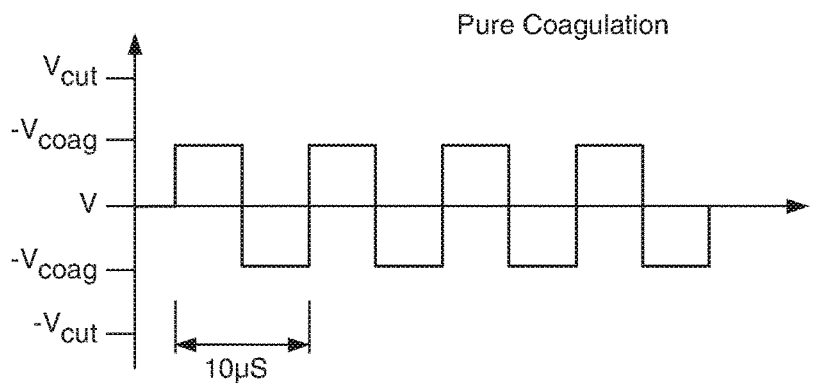
Figure 11C:
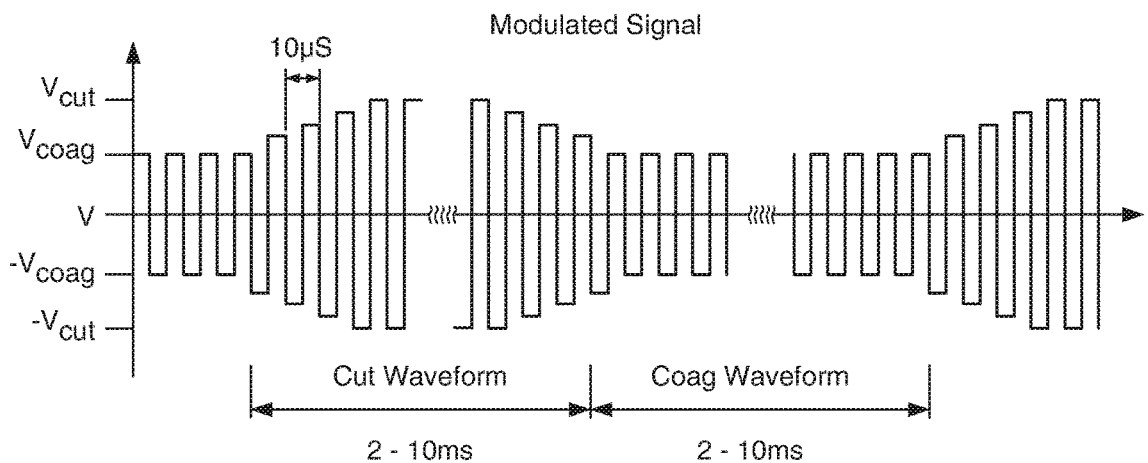

Another example mode, briefly described earlier, is a pulsed or modulated output that may by achieved with a single RF generator, similar to that described in FIG. 9, or may be delivered on the cutting blade or electrode, while simultaneously providing hemostasis by way of a second electrode using a dual RF generator system as described in FIG. 10. Pulsing or voltage modulation is represented in FIG. 11C and represents an example of a modulated voltage provided to at least one electrode, which may be modulated between a high voltage period (i.e., sufficient to initially create an ionized vapor layer and then a plasma) and a low voltage period (i.e., insufficient to maintain the plasma). The time of the pulsing may be adjustable and dependent on preferences of the surgeon (e.g., 10 milliseconds (ms) of high voltage and 10 ms of low voltage, 5 ms on and 5 ms off, etc.), but generally the slower the pulsing the slower the cutting action provided. It is noted that the pulsing described in this section is a pulsing of the RF energy provided to the cutting electrode, which RF energy is applied in the form of a square wave (e.g., 50% duty cycle) at 100 kilohertz, so the pulsing should not be confused with the square wave application of RF energy. Shown in FIG. 11A is the more typical square waveform at a cutting or ablating voltage, at an exemplary 100 KHz, between 180 and 320V, that will generally form plasma at an electrode with a configuration such as active electrodes described herein. Shown in FIG. 11B is an exemplary square waveform at a coagulating or hemostatic voltage, alternating at an exemplary 100 KHz, between 40-120V, that will generally not form a plasma at an electrode similar to active electrodes described herein but seal smaller blood vessels and coagulate tissue in the local area. Pulsing of this RF energy is shown in FIG. 11C, wherein a cutting voltage is supplied for a first period of time and then a coagulating voltage is supplied for a second period of time, these first and second periods of time may be approximately equivalent, but may be different to each other depending on the desired tissue effect. For example, a longer cutting period relative to a coagulating period tends to provide more plasma generation and cutting tissue effects with reduced hemostasis. The reverse ratio, with a longer period of time at a coagulating voltage relative to an ablating voltage would provide more hemostasis with slower cutting. For example, the inventors have found that a cutting period of 8 ms, with a coagulating period of 2 ms provided strong cutting with minimal hemostasis, while the reverse provided minimal cutting with strong hemostasis. Of note in FIG.

11C, the first and second periods of time are shown truncated, to simplify the representation. In reality, there would be many more (thousands more) square wave oscillations in each period given an AC signal in the order of 100 KHz, modulating with a 10 ms high voltage period.

Moreover, and as alluded to in the previous paragraph, the pulsing is between a high voltage and a lower voltage, but not preferably zero volts. The inventors have found that pulsing between a high voltage in the range of 200-320 volts and lower voltage in the range of 10-150 volts was preferable. For the embodiments described herein, pulsing between a high voltage in the range of 250-300 volts and lower voltage in the range of 30-70 volts was more preferable, the values adjusting depending on levels of desired cutting and concomitant thermal effect. For example, pulsing between 300 volts and 70 volts would provide both aggressive cutting and hemostasis, while pulsing between 300 and 30 volts would provide aggressive cutting and reduced hemostasis. These values may vary with electrode configuration.

The theory of operation is that by pulsing, not only does the plasma extinguish (which reduces molecular disassociation and thereby the cutting action), but the vapor layer also collapses, and when the voltage rises again higher current is dissipated until the vapor layer is formed, creating more significant thermal effects and therefore provide the hemostasis. Thus, in addition to modifying the ratio of periods of time between the first cutting voltage and the second coagulating voltage, the amount of hemostasis provided from the cutting electrode is dependent to some extent upon the "low" voltage. A simultaneous hemostasis associated with a second electrode in the example dual RF system may also provide additional multipolar blended hemostasis along the wand tip. There may be advantages to using a fast pulse rate (e.g., less than 5 ms in high or low voltage) to reduce the audible and tactile nature of the pulse—or perhaps the audible and tactile feedbacks could be desirable to hear and feel for certain applications. It can be tailored to the needs of the procedure and tissue type. There could also be a randomly assigned high/low voltage duration that averages out to a desired duty cycle, such as 70% high voltage, 30% low voltage, but individual cycles may vary. This may create more of an audible "white noise" effect that hides the repetitive pulsed nature that some users may not prefer.

Modes of Operation

In example systems, the user may select "Modes" of energy output that set RF generator(s) output of the controller to pre-set output energy levels and to specific terminals depending on the instrument that is coupled to the controller. The controller may also control the rate and location of fluid delivery and fluid aspiration to and from the wand tip, in conjunction with the selectable energy outputs, and certain tissue modes or selections made by the user may trigger certain pre-set fluid flow rates to further improve the tissue effect.

For example, the controller may have a "tonsil mode." In tonsil mode, if the user wishes for reduced hemostasis the user may select a pure cut mode (pure ablation mode) with a medium cutting speed, and a low fluid delivery flow rate. The selection may, for example, couple a first RF generator to an active and return electrode (e.g., an active electrode configured for fine dissection), with the RF generator controlled so as to supply energy sufficient to form plasma and finely dissect tissue. Selecting a blend cut mode or a hemostatic cut mode however may initiate a pulsing of the first RF generator in which the first RF generator modulates between supplying energy sufficient to form a plasma and then reducing voltage to enable the plasma to collapse, with the pulsing providing an initial heating effect while the plasma is forming and some hemostasis. As explained earlier, varying levels of cutting and hemostasis may be achieved with corresponding ratios between the cutting and hemostatic periods of the pulsing duty cycle. Alternatively or in addition to pulsing with a first RF generator, selecting a blended cut may optionally trigger energy supplied to a secondary electrode from a second RF generator (for multipolar wands coupled to a dual RF generator system) triggering a multipolar blend cut mode, the second RF generator programmed to supply an energy that coagulates tissue around the secondary electrode pair. Each mode selection may also alter the irrigation or aspiration level to and from the tissue and wand. An example Tonsil Mode chart is shown below.

When larger vessels are encountered, the wand may be rotated so as to place a different portion of an electrode, or a second active electrode adjacent the vessel and a pure coagulation mode may be selected, where no ablation is desired. Fluid delivery may be reduced during pure coagulation mode compared to ablation and blended modes.

| "Tonsil" Mode | When to Use | Adjustable Cutting Speed |
| --- | --- | --- |
| Pure Cut - Low thermal effect, low hemostasis | Patients with small anatomy & vascularity Procedures needing preservation of adjacent structures and minimal thermal effect | Hi Med Low |
| Blend Cut - High thermal effect, high hemostasis | Patients with larger anatomy & vascularity Procedures needing maximum hemostasis during dissection | Hi Med Low |
| Pure Coagulation | Target bleeding vessels | Low Med High |

Another envisioned mode may be an "adenoid mode" that automatically couples an electrode configured to debulk tissue to an active terminal of a first RF generator. The user may select a debulking speed that may operate so as to increase a variable associated with electrical field intensities (e.g., voltage at an electrode configured to debulk tissue) to a pre-set value programmed within a memory of the controller. Adenoid mode may also set the fluid delivery pump of the controller to a pre-set rate that may be higher than tonsil mode, so as to aid the flow of fluid around the wand distal tip and support flow of the treated tissue through an aspiration aperture. Adenoid mode may disconnect at least one pin of a controller connector so that only one RF generator is electrically coupled to an electrode pair. An example Adenoid Mode chart is shown below.

| "Adenoid" Mode | When to Use | Adjustable Debulking Speed |
| --- | --- | --- |
| Debulking Action - Rapid removal of adenoid tissue | Adenoidectomy Surface debulking of tissue Possible use for intracapsular tonsillotomy. | Hi Med Low |

In alternative embodiments, a simplified set of modes may be offered, including high and medium ablation modes, and pure coagulation, the latter being similar to that described above.

| Mode | Description | Adjustments |
| --- | --- | --- |
| Ablation High | Tissue debulking at high, medium or low speeds. | High<br>Medium<br>Low |
| Ablation Medium | Tissue dissection, adjustable for varying blend ratios, adjusting speed of cutting and concomitant hemostasis. | High<br>Medium<br>Low |
| Coagulation | Tissue coagulation | |

For example, the controller may have a "high ablation" mode that may operate similarly to the adenoid mode described earlier. The user may select a debulking speed within the high ablation mode that alters a variable associated with electrical field intensities (e.g., voltage at an electrode configured to debulk tissue) to a pre-set value programmed within a memory of the controller. This high ablation mode may also set the fluid delivery pump of the controller to a pre-set rate that may be higher than other modes, so as to aid the flow of fluid around the wand distal tip and support flow of the treated tissue through an aspiration aperture. This mode may disconnect at least one pin of a controller connector so that only one RF generator is electrically coupled to an electrode pair.

Medium mode may provide options similar to the tonsil mode described earlier. The selection may, for example, couple a first RF generator to an active and return electrode (e.g., an active electrode configured for fine dissection), with the RF generator controlled so as to supply energy sufficient to form plasma and finely dissect tissue. Adjusting the level higher in medium mode may provide a purer cut mode, with less concomitant hemostasis, while adjusting the level lower may provide a more hemostatic cut mode; such as a pulsing of the first RF generator in which the first RF generator oscillates between supplying energy sufficient to form a plasma and then reducing voltage to enable the plasma to collapse, with the pulsing providing an initial heating effect while the plasma is forming and some hemostasis. Further example of blending cutting and hemostasis using a multipolar configuration may also be triggered, as described earlier in the instant specification. Each mode selection may also alter the irrigation or aspiration level to and from the tissue and wand.

Alternative Use Wands Wand Tip Embodiment

The following embodiments show an alternative set of wand-tip embodiments configured for more general procedures, providing a variety of tissue effects including both hemostasis and cutting for other procedures, such as arthroplasty and general surgery procedures. Similar to previous embodiments, these forthcoming wand-tip embodiments have a cutting or blade style portion to provide a cutting tissue effect and may have an electrode to provide concomitant hemostasis. The example systems also comprise tripolar or multi-polar wands having at least three electrodes. By way of the controller, each electrode may be interchangeably connected to at least one active and one return terminal of an RF generator of the controller similar to some embodiments described earlier. Thus, each electrode may be an active electrode, a return electrode, or floating for any particular surgical procedure.

Sixth Wand-Tip Embodiment

Figure 12:
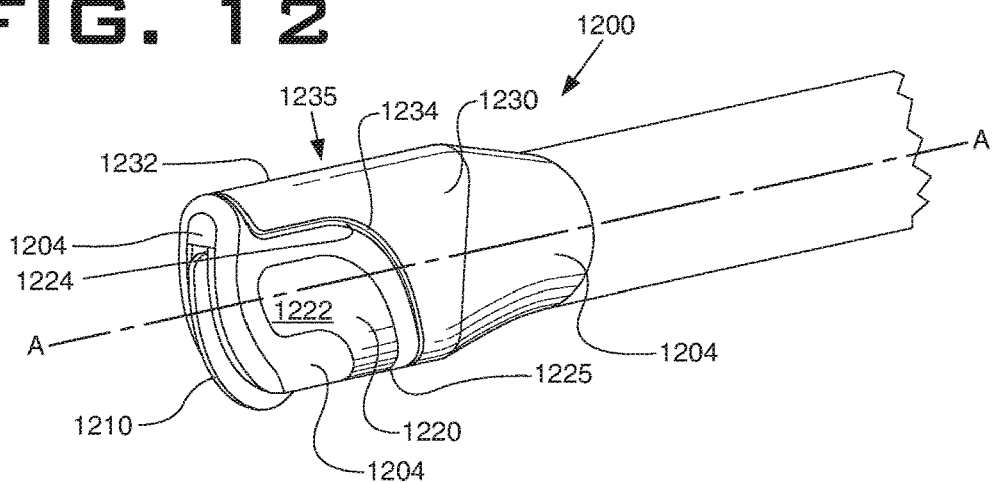
FIG. 12 shows a perspective view of the distal tip of a sixth wand-tip embodiment in accordance with at least some embodiments of the disclosure.

FIG. 12 shows a perspective view of a sixth wand-tip embodiment 1200. Similar to some earlier described embodiments, each electrode may be interchangeable as an active or return electrode. In some embodiments, the cutting electrode 1210 is the active electrode. The example cutting electrode 1210 may be a thin plate or scalpel shaped electrode, having sharper corners or edges configured to enhance plasma initiation and improve cutting, dissection, or dissociation of tissue. The cutting electrode 1210 may also include holes therethrough (not specifically shown) such that, if operated in a coagulation mode, the holes may fill with fluid to improve the thermal effect. Cutting electrode 1210 extends parallel to the longitudinal axis and as shown, bifurcates a thickness of the wand tip. Blade electrode 1210 extends along and around the distal end of spacer 1204, so as to cross over the longitudinal axis A-A at the distal tip. Stated otherwise the blade distal-most edge extends along a first side of the wand and around the spacer distal-most end, so as to be disposed on both sides of the longitudinal axis. Stated otherwise if a first and second plane defines two perpendicular planes, both parallel and coincident with the wand longitudinal axis, the blade electrode is disposed symmetrically around the first plane, and asymmetrically disposed around the second plane. In example embodiments, the cutting electrode 1210 and second electrode 1220 may be sized so that combined they provide approximately the same surface area as third electrode 1230 causing a symmetrical current flow situation in certain configurations.

In some modes third electrode 1230 may be the coagulation electrode since third electrode 1230 is larger in size (surface area) than the cutting electrode 1210, and third electrode 1230 has a smooth rounded surface to coagulate a target tissue. In other modes second electrode 1220 may be the coagulating electrode. In yet still other modes, third electrode 1230 may be a debulking electrode around which ionized vapor and plasma may be formed. Second electrode 1220 may be a return electrode to provide a return path for both the cutting and coagulating electrode.

Second and third electrode may be shaped and positioned on the wand so as to maintain as consistent a distance from any edge of the intended active electrodes as possible. Second electrode 1220 may act as a return electrode at times or an active electrode at times. A consistent distance is generally thought to maintain a more consistent tissue effect along the length of an active electrode. Therefore distal edge of second electrode 1220 is curved so as to approximately follow the curved distal portion of blade electrode 1210, and a distal edge 1234 of third electrode 1230 curves so as to approximately follow and maintain a uniform distance from proximal edge 1224 of second electrode 1220. Second and third electrode define conforming electrode that wrap around the wand distal end and the rear view of wand 1200 (not shown) is a mirror image of the front view. The second electrode 1220 wraps around a bottom surface 1225 of the wand distal end while the third electrode wraps around both a top surface 1235 and bottom surface 1225, the third electrode top portion coinciding with the top surface 1235 defining a distally extending notch 1232. Second electrode 1220 also has a distally extending notch portion 1222 extending along the longitudinal axis and along both sides of the wand distal end.

Seventh Wand-Tip Embodiment

Figure 13A:
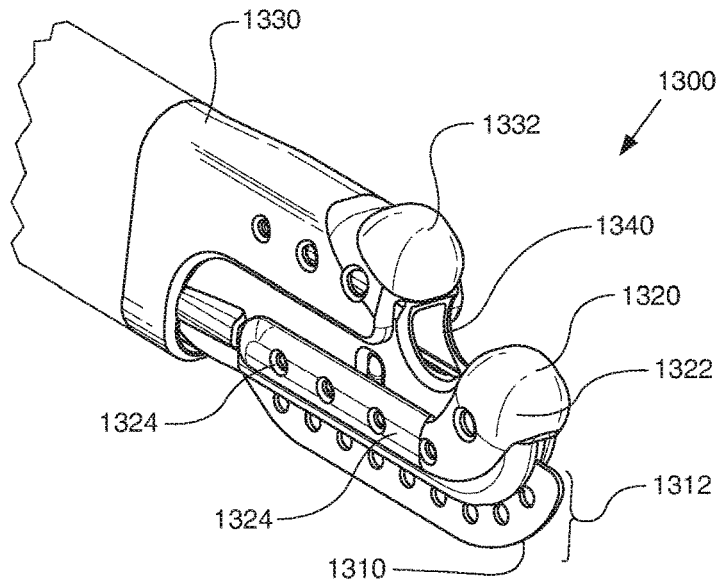
FIGS. 13A and 13B show a perspective and a side view of the distal tip of an seventh wand-tip embodiment in accordance with at least some embodiments of the disclosure.
Figure 13B:
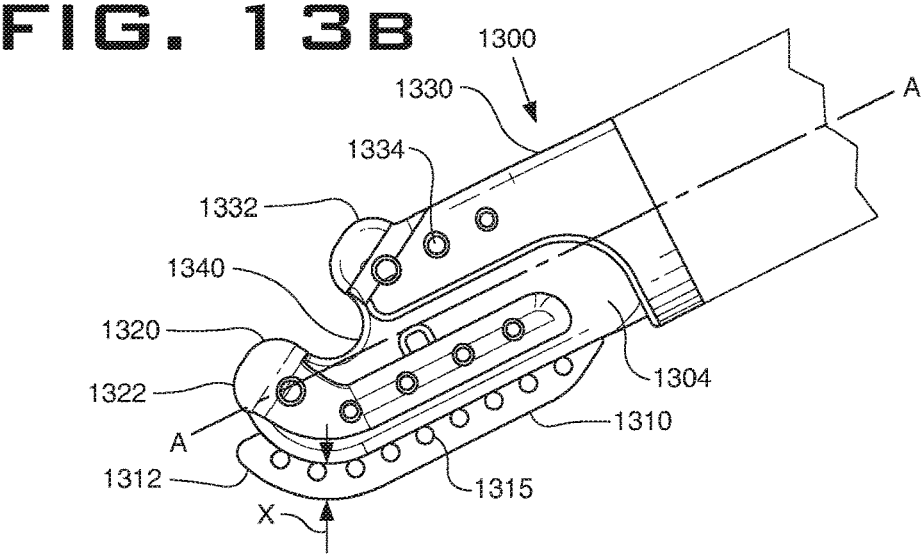

FIGS. 13A and 13B shows a perspective end view and a side elevation view of a seventh wand-tip embodiment respectively, in accordance with example embodiments. This embodiment may be particularly useful in open procedures, when incising skin or through soft tissue, such as arthroplasty procedures. As shown, this wand-tip embodiment includes three electrodes. The primary electrode 1310 is an elongated blade style electrode. The narrow geometry creates high field intensities at the distal edge surface to form plasma configured to molecularly dissociate tissue and perform a tissue cutting function. A plurality of holes 1315 along the primary electrode (if and when present) may provide additional focus points for the current density field to improve cutting. The plurality of holes 1315 may be omitted in other embodiments. The primary electrode 1310 extends from the spacer 1304 both distally and laterally and extends along a length of the distal tip. Primary electrode 1310 does not extend around the tip so as to cross the longitudinal axis A. Shown here, primary electrode 1310 has an approximately uniform dimension X. In alternative embodiments the distal portion 1312 of primary electrode may have a gradually increasing dimension X, so that the distal portion 1312 has a larger surface area for improved performance in the coagulation mode.

The return electrode 1320 extends along the wand distal end, maintaining an approximately consistent distance from the primary electrode 1310, including a curve at the distal portion so as to terminate in a rounded, spherical or bulbous end 1322 that is at an angle to a long axis of the wand. In the embodiments of FIGS. 13A and 13B, the return electrode 1320 may be symmetrical, and may have the same shape on each side of the spacer 1304. Apertures 1324 through the return electrode (as shown, five such apertures on each side) may be fluidly coupled to a fluid flow element along the wand shaft, similar to embodiments described earlier provide a conduit for fluid flow. In some embodiments, fluid is delivered through the apertures 1324 in both the return electrode 1320 and secondary electrode 1330, supplied through independent fluid channels within the wand, or through a single fluid delivery element, split within the wand a sufficient distance from the electrodes so as to avoid a low resistance internal electrically conductive path through the electrically conductive fluid within the wand, as described in earlier embodiments. Fluid and debris may be aspirated through the aperture 1340 in the spacer that opens between the bulbous ends 1322 and 1332 of the return and secondary electrodes.

The secondary electrode 1330 defines an upper surface of the wand distal tip, and the secondary electrode 1330 may be a distal portion of a wand shaft that encircles the wand distal end (as shown). The secondary electrode 1330 may terminate at the distal tip with a rounded or bulbous end 1332 disposed at an angle to the long axis (A-A) of the wand and parallel but spaced away from the return electrode terminus 1322. The secondary electrode 1330 may include a plurality of apertures 1334 (as shown, three on each side) fluidly coupled to a fluid flow element associated with the wand, the apertures 1334 operable to flow a fluid, and preferably to deliver an electrically conductive fluid. Fluid delivery apertures 1324 and 1334 may be disposed on the same side of the wand. As shown a plurality of fluid delivery apertures are disposed on both sides of both the return electrode 1320 and secondary electrode 1330; however the plurality of fluid delivery apertures may in some embodiments only be present on a single side.

Disposed between the two bulbous distal tips 1322 and 1332 of the secondary and return electrodes is an aperture 1340 defines by the spacer 1304, the aperture 1340 configured to aspirate fluid and plasma by-products. Wand distal end is preferably not circular but has a cross section with a smaller width than height. This keeps the instrument smaller, and improves access to tissues and visibility to the target site. As such both the return electrode and the secondary electrode are disposed on both sides, while the primary electrode 1310 bifurcates the width, disposed along the longitudinal axis A.

In use, the primary electrode 1310 may be supplied with a specific energy output to generate plasma and provide a cutting operation through tissue. When used in a tri-polar mode, the secondary electrode 1330 may be supplied a specific energy to coagulate tissues proximate to the secondary electrode 1330. The inventors envision that while the user begins to cut into tissue, minimal hemostasis may be initially required up until a certain depth of tissue, and as the primary electrode 1310 cuts deeper more hemostasis may be required. Therefore as the blade goes deeper in the tissue, the secondary electrode will naturally begin to approach tissue and become operable to coagulate, as a result of the secondary electrode's location relative to the tissue, the tissue acting as a bridge to the electrical current path. In an alternative use, the primary electrode 1310 may be supplied with a specific energy output to generate plasma and provide a cutting operation through tissue, with only the return electrode 1320 electrically coupled to an output of the controller, and upon some hemostasis being required, the output may be changed to an energy output, between the same primary and return electrodes (1310 and 1320) that coagulates tissue; an output with lower voltage, and may also be power controlled.

The instrument of FIGS. 13A and 13B is further configured to provide broad surface area coagulation, with little to no cutting. During coagulation, the primary cutting electrode may or may not be selectively uncoupled or floated from the RF generator. The instrument may be rotated to a second orientation, so as to place both spherical tips (ends or return and secondary electrode 1320 and 1330) onto or buried into tissue while supplying an electrically conductive fluid through at least one of the apertures 1334, 1324 at the wand distal tip. At this point, the surface area in contact with tissue is approximately equal and energy supplied performs a hemostatic effect, such as a sine waveform, low voltage, and constant power control. In other embodiments, an additional set of "forward-facing" apertures for saline delivery underneath the most distal bulbous tip may be used to provide more directed flow to the distal tip of the cutting electrode (1312). Such "forward-facing" apertures may enable a lower overall flow rate to be used, since plasma will be able to more easily generate at the initial point of contact with tissue and also result in less pooling of saline around the tip during use. It may also help minimize a thermal blanching effect on initial tissue contact that sometimes happens when there is a brief resistive heating period on tissue contact before plasma forms. This device therefore may have a variety of modes, potentially utilizing many output parameters such as number of RF generators; pulsing outputs at varying duty cycles and frequencies, tripolar or bipolar modes, voltages and control modes (power control versus voltage control). In addition, the fluid flow may also have pre-set values for each mode, for example the fluid delivery may be lower during coagulation only mode than during cut mode. In some modes the fluid delivery or suction may adjust output based on electrical readings. For example, a higher impedance reading may indicate a drier environment, and thereby sending a signal so as to boost pump speed and thereby fluid delivery to compensate. The inventors also envisioned sensing an electrical parameter, such as impedance between the an electrode pair pre-activation, and if the impedance is too low, increase pump speed and thereby fluid delivery for a set period of time before delivering energy to improve an electrical current pathway between the electrode pair. This may ease startup, provide smoother dissection, and less thermal effect, or reduce hot spots.

| Mode | Example Configuration |
|---|---|
| PURE CUT MODE | 1 RF generator, coupled to electrode 1310 and 1320, Voltage control output sufficient to generate plasma |
| CUT MODE SOME HEMOSTASIS | 1 RF generator, coupled to electrode 1310 and 1320, pulsing output control. 2 RF generators, 1 coupled to electrode 1310 and 1320, voltage control output sufficient to generate plasma, the other RF generator coupled to electrodes 1320 and 1330, power output control to coagulate. 2 RF generators, 1 coupled to electrode 1310 and 1320, pulsing output sufficient to sometimes generate plasma, the other RF generator coupled to electrode 1320 and 1330, power output control to coagulate. |
| COAG MODE | 1 RF generator, coupled to electrode 1310 and 1320, power output control, coagulation voltage output. 2 RF generators, 1 coupled to electrode 1310 and 1320 pair, coagulation output, the other RF generator coupled to electrodes 1320 and 1330, coagulation output. |

Alternatively, in a similar fashion to the tonsil and adenoid mode described earlier, alternative tissue-centric modes have also been envisioned for these later described embodiments. For example, a "Skin mode" may offer a tissue effect with low thermal effect, moderate ablation for easy cutting without peripheral damage and may be akin to a "tonsil mode" or a pure cutting mode in the table above. A "Capsule/connective tissue" mode may provide moderate thermal effect and high ablation to cut through more difficult tissues where some thermal effect is acceptable, and "muscle" mode which may provide a blended or pulsed activation to deliver high thermal effect while dissecting vascular tissues.

Eighth Wand-Tip Embodiment

Figure 14A:
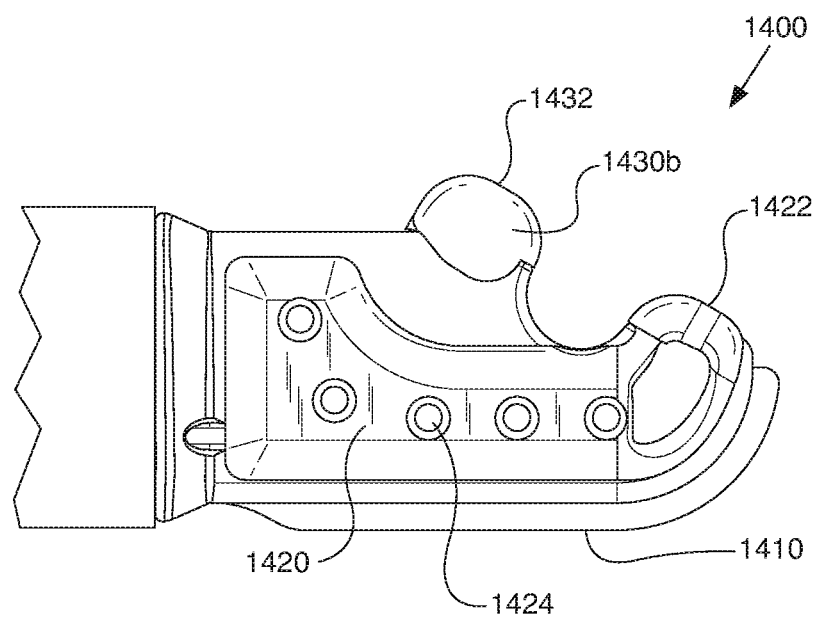
FIGS. 14A and 14B show a left and right side view of the distal tip of an eighth wand-tip embodiment in accordance with at least some embodiments of the disclosure.
Figure 14B:
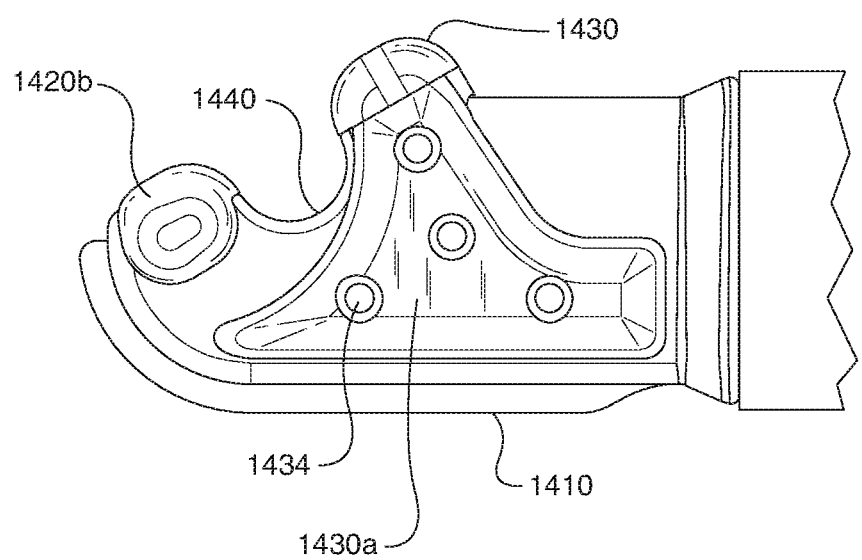
Figure 14C:
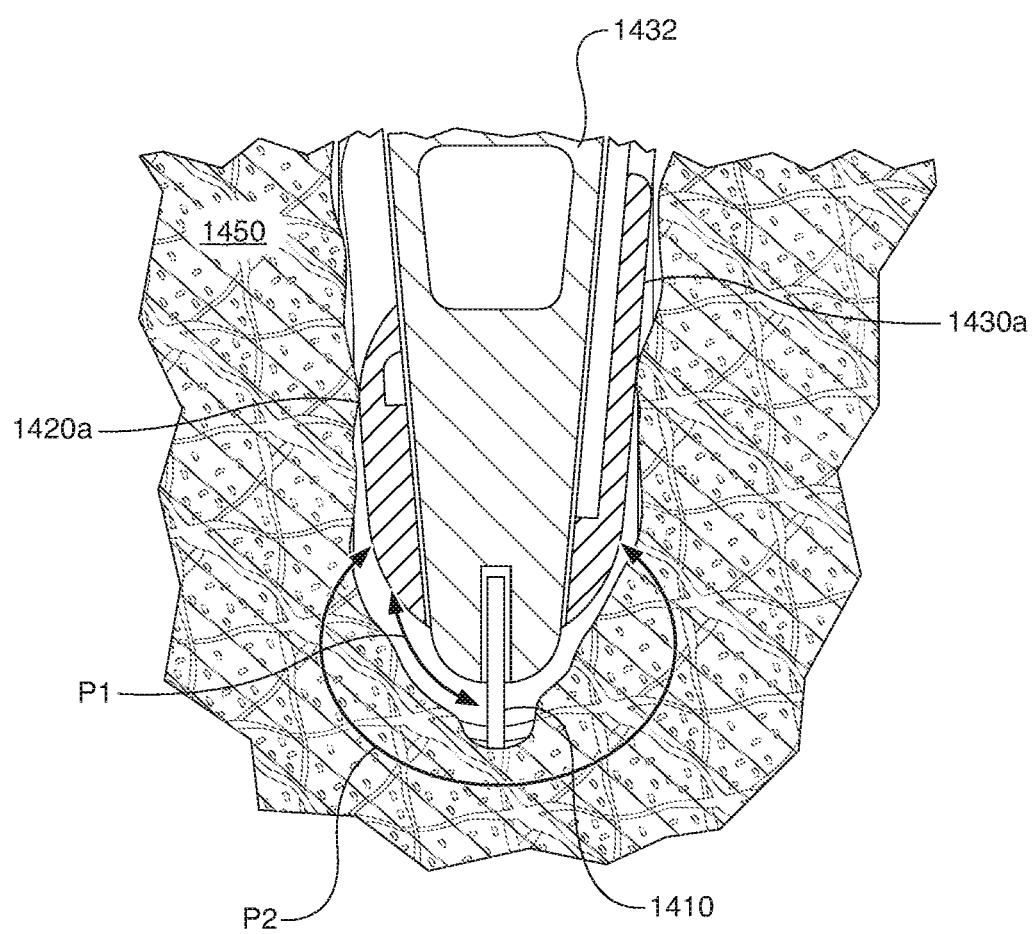
FIG. 14C shows a cross-section of the eighth wand-tip embodiment in accordance with at least some embodiments of the disclosure.

FIGS. 14A, 14B and 14C shows a left, right side elevation views and a cross sectional representation respectively of the distal end of another wand in accordance with example embodiments and similar to that shown in FIGS. 13A and 13B. An element of the design of FIGS. 14A and 14B is the asymmetrical nature of the return and secondary electrodes. In addition, the primary or blade electrode 1410 in the example systems has no apertures in the example system, but the presence of absence of apertures in the blade electrode 1410 is not tied to the asymmetric nature of the return and secondary electrodes of FIGS. 14A and 14B. As shown, the return electrode 1420 is asymmetric, defining two return electrode sides 1420a and 1420b, the first side 1420a significantly larger in surface area than the second side 1420b. The example wand tip of FIGS. 14A and 14B further comprises a secondary electrode 1430 defining a first and second side 1430a and 1430b respectively, the first side 1430a significantly larger in exposed surface area than the second side 1430b, the first side 1430a on the opposite side to the return electrode first side 1420a. Stated otherwise the larger portion of the secondary electrode (1430a) is on an opposite side to the larger portion of the return electrode 1420a.

The asymmetry enables the secondary electrode 1430 to contact tissue closer to the tip of the device. The asymmetry also pushes the energy around the tip of the device creating a thermal effect around the cut rather than just on the sides. In example cases the surface area of the return and secondary electrodes are sized so as to balance the thermal effect on each side of the cut. The design of FIGS. 14A and 14B could be effectively used with the pulsed mode to create a more evenly distributed thermal effect along the sides and bottom of the cut. The distance between the return and secondary electrodes are large enough to allow electricity to flow around the cutting blade, represented in FIG. 14C.

In use, conductive fluid is delivered through the apertures 1424 and 1434 in both the return and secondary electrodes. As shown, the return electrode 1420 has five apertures out which fluid flows (FIG. 14A), and the secondary electrode 1430 has four apertures 1434 arranged in something of triangular shape and out which fluid flows (FIG. 14B). Aspiration occurs through an aperture 1440 in the spacer, with the opening being located between the bulbous ends 1422 and 1432.

FIG. 14C shows a cross section of wand embodiment 1400. During cut mode only, electrode pair 1410 and 1420 may be coupled only, and a current path (P1) is maintained between the electrode 1410 and 1420. In coagulation mode, or multipolar blend mode for the same wand orientation, a current path (P2) also may exist (in addition to P1 in multipolar blend mode) through the tissue 1450 to coagulate tissue. In both these last two wand-tips embodiment, separate fluid channels coupled to the apertures may be provided along the length of the elongate shaft (only partially visible in the figures) to obviate the possibility a bypass electrical current path through the flowing fluid within the shaft.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. An electrosurgical wand, comprising:
    a handle on a proximal end of the electrosurgical wand and an elongate shaft coupled to the handle and extending distally from the handle along a longitudinal axis;
    a combination active electrode having a blade portion and a screen portion disposed on a distal end of the electrosurgical wand, wherein the blade portion extends along and laterally from the electrosurgical wand longitudinal axis defining the distal-most portion of the electrosurgical wand, and wherein the screen portion forms an obtuse angle to the blade portion, the obtuse angle opening toward the distal end of the electrosurgical wand and has at least one aperture therein fluidly coupled to an aspiration channel within the electrosurgical wand; and second and third electrodes, proximally spaced from the combination active electrode, the second electrode spanning a portion of an outside surface of the electrosurgical wand adjacent and proximally spaced from the blade portion of the combination active electrode, the third electrode spanning a portion of the outside surface of the electrosurgical wand opposite the second electrode.

2. The electrosurgical wand of claim 1, wherein the second electrode defines a thermal electrode.

3. The electrosurgical wand of claim 1 wherein the second and third electrodes are two discrete portions of a single electrode element separated by an insulating portion.

4. The electrosurgical wand of claim 1, wherein the second electrode spans a single side of the electrosurgical wand, and the third electrode spans at least three sides of the electrosurgical wand.

5. The electrosurgical wand of claim 1, wherein an insulative spacer is disposed between the combination active electrode, the second electrode and the third electrode and has a distal planar surface oriented at an obtuse angle to the longitudinal axis and parallel with the obtuse angle of the screen portion.

6. The electrosurgical wand of claim 1, wherein the screen portion further comprises a surface asperity configured to more readily form plasma adjacent the surface asperity.

7. The electrosurgical wand of claim 1, wherein the second and third electrodes are axially offset from each other, so that a distal edge of the second electrode extends further axially than a distal edge of the third electrode.

8. The electrosurgical wand of claim 7 wherein the distal edges of the second and third electrodes lie along a plane that is parallel to the screen portion.

9. The electrosurgical wand of claim 1, wherein the second electrode has a smaller surface area than the third electrode.

10. The electrosurgical wand of claim 1 wherein the second electrode has a plurality of axially spaced apertures therethrough, and the third electrode has a plurality of radially spaced apertures therethrough, both pluralities of apertures in fluid communication with a fluid delivery channel within the electrosurgical wand.

11. The electrosurgical wand of claim 1, wherein the second electrode has a polished surface finish configured to reduce tissue sticking, and the third electrode has an unpolished surface finish, configured to improve surface fluid retention.

12. A system comprising:
an electrosurgical controller comprising a processor;
a memory coupled to the processor;
a voltage generator operatively coupled to the processor, the voltage generator comprising an active terminal and a return terminal;
a wand connector configured to couple to a connector of an electrosurgical wand, and the wand connector comprising a plurality of electrical pins, and at least one electrical pin coupled to the active terminal of the voltage generator; and
a peristaltic pump comprising a rotor coupled to an electric motor, the electric motor operatively coupled to the processor; and
an electrosurgical wand comprising:
a handle and an elongate shaft extending distally from the handle along a longitudinal central axis;
a combination active electrode disposed at a distal end of the electrosurgical wand defining a blade portion at the distal-most end of the electrosurgical wand extending along and laterally offset from the longitudinal central axis and a screen portion having at least one aperture in operational relationship to a fluid channel within the electrosurgical wand therethrough;
a return electrode abutting the elongate shaft and extending along and annularly about the longitudinal central axis, having first and second exposed portions that are distinct from each other, the first exposed portion extending along a first side of the elongate shaft adjacent the blade portion of the combination active electrode and the second exposed extending along an opposing side of the elongate shaft; and wherein the memory stores a program that, when executed by the processor, causes the processor to implement at least two modes of ablation during an electrosurgical procedure;
wherein in a first mode of the at least two modes of ablation, the program causes the processor to:
control flow of fluid though an aperture that is proximate to the return electrode on the distal end of the electrosurgical wand at a first flow rate; and
control energy delivered to the combination active electrode by the electrosurgical controller so as to molecularly dissociate tissue with minimal hemostasis; and
wherein in a second mode of the at least two modes of ablation, the program causes the processor to:
control flow of fluid through the aperture that is proximate to the return electrode on the distal end of the electrosurgical wand at a second flow rate different than the first flow rate; and
control energy delivered to the combination active electrode by the electrosurgical controller so as to molecularly dissociate tissue with more hemostasis.

13. The system of claim 12 wherein the processor is further configured to control the energy so as to molecularly dissociate tissue by pulsing a voltage output between a voltage sufficient to form an ionized vapor layer adjacent the combination active electrode and a voltage sufficient to extinguish the ionized vapor layer.

14. The system of claim 13 wherein the processor is further configured to control the energy so as to molecularly dissociate tissue by pulsing the voltage output at a first pulsing rate in the first mode and at a second pulsing rate, different from the first pulsing rate, in the second mode.

* * * * *